United States Patent [19]
Gilbert et al.

[11] Patent Number: 5,904,652
[45] Date of Patent: May 18, 1999

[54] ULTRASOUND SCAN CONVERSION WITH SPATIAL DITHERING

[75] Inventors: Jeffrey Gilbert, El Cerrito, Calif.; Alice M. Chiang, Weston; Steven R. Broadstone, Woburn, both of Mass.

[73] Assignee: TeraTech Corporation, Burlington, Mass.

[21] Appl. No.: 08/773,647

[22] Filed: Dec. 24, 1996

Related U.S. Application Data

[63] Continuation-in-part of application No. PCT/US96/11166, Jun. 28, 1996, which is a continuation-in-part of application No. 08/599,816, Feb. 12, 1996, Pat. No. 5,690,114, which is a continuation-in-part of application No. 08/496,804, Jun. 29, 1995, Pat. No. 5,590,658, and application No. 08/496,805, Jun. 29, 1995.

[51] Int. Cl.⁶ ..................................................... A61B 8/00
[52] U.S. Cl. ............................................................ 600/447
[58] Field of Search ........................ 128/660.07, 660.08, 128/661.01, 662.03, 662.06; 73/625, 626, 628; 382/254, 260, 270; 600/444, 445, 446, 447, 459, 462, 463

[56] References Cited

U.S. PATENT DOCUMENTS

| | | | |
|---|---|---|---|
| 3,953,668 | 4/1976 | Judice | 178/6 |
| 4,092,867 | 6/1978 | Matzuk | 73/609 |
| 4,689,675 | 8/1987 | Tchorbajian et al. | 358/140 |
| 5,109,282 | 4/1992 | Peli | 358/298 |
| 5,272,627 | 12/1993 | Maschhoff et al. | 364/413 |
| 5,286,964 | 2/1994 | Fountain | 250/201 |
| 5,355,303 | 10/1994 | Ferla et al. | 346/107 |
| 5,369,497 | 11/1994 | Allen et al. | 358/298 |
| 5,406,949 | 4/1995 | Yao et al. | 128/662 |
| 5,477,305 | 12/1995 | Parker et al. | 358/456 |
| 5,479,594 | 12/1995 | Lum | 395/143 |
| 5,543,941 | 8/1996 | Parker et al. | 382/270 |

OTHER PUBLICATIONS

Richard, William D. and Arthur, R. Martin, "Real–Time Ultrasonic Scan Conversion Via Linear Interpolation of Oversampled Vectors", Ultrasonic Imaging 109–123 (1994).

*Primary Examiner*—George Manuel
*Attorney, Agent, or Firm*—Hamilton, Brook, Smith & Reynolds, PC

[57] ABSTRACT

An ultrasound imaging system includes a scan conversion process for converting ultrasound data into a standard display format conversion and can be performed on a personal computer by programming the computer to convert data from polar coordinates to Cartesian coordinates suitable for display on a computer monitor. The data is provided from scan head enclosure that houses an array of ultrasonic transducers and the circuitry associated therewith, including pulse synchronizer circuitry used in the transmit mode for transmission of ultrasonic pulses and beam forming circuitry used in the receive mode to dynamically focus reflected ultrasonic signals returning from the region of interest being imaged.

42 Claims, 23 Drawing Sheets

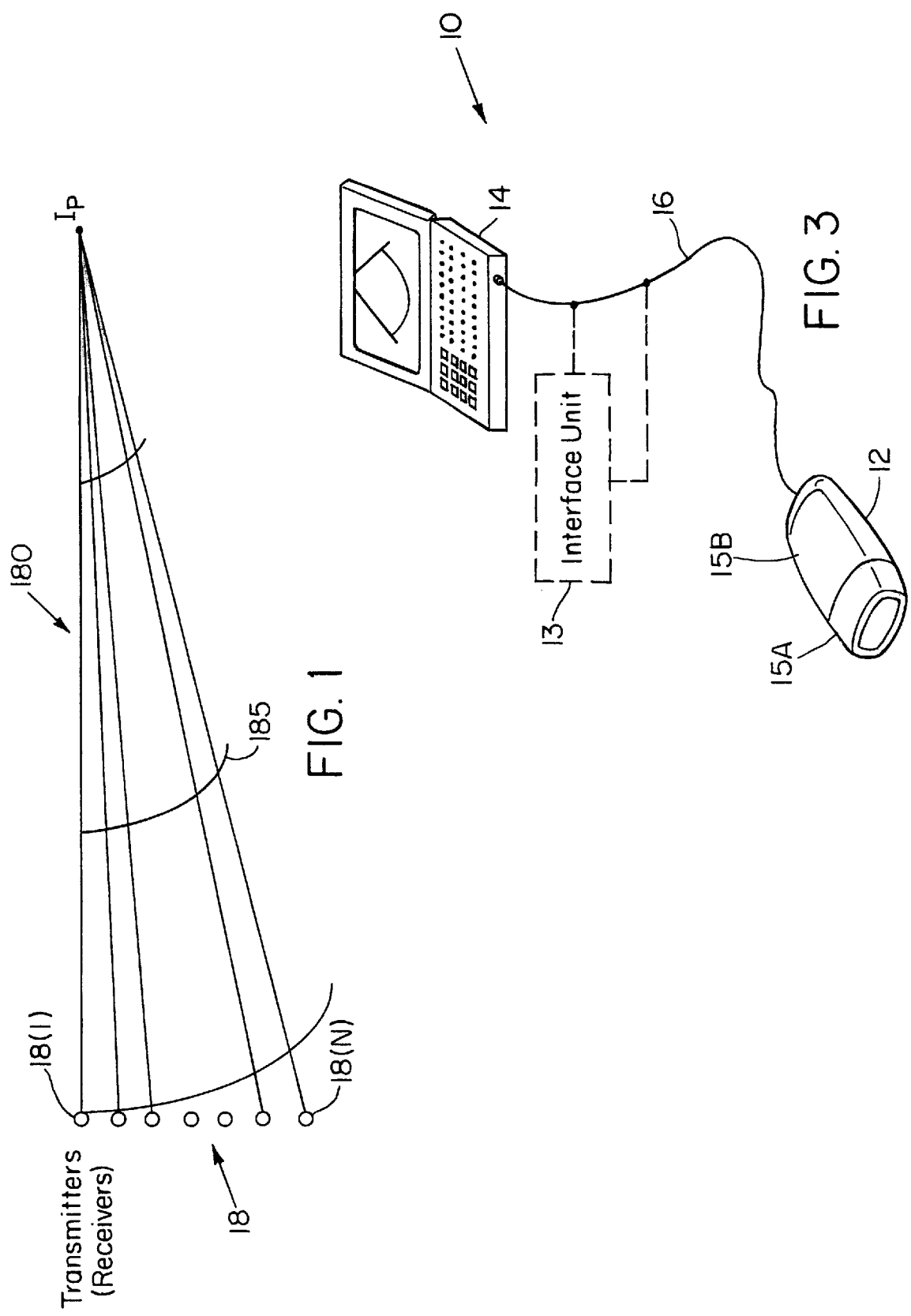

| Model Type | Safety Info | Image IPA Data | Doppler IPA Data | Color IPA Data | Probe Geometry | In |

Probe 770-0011-00 – Probe Model Properties

General Settings

Biopsy Enable: FALSE
Center Line Def: 4530
Rline Correction: 16
Lens Thickness (mm): 130
Probe Style: CRVED
Xducer Freq.(kHz): 3750
RFP Attenuation: -6dB OK   Cancel   Apply Press Ctrl TAB to go to the next property page
Press Ctrl Shift TAB to go to the previous property page

FIG. 14A

Probe 770-0011-00 - Probe Model Properties

| Model Type | Safety Info | Image IPA Data | Doppler IPA Data | Color IPA Data | Probe Geometry | In ▲▼ |

General Settings

Aperture: 0    I Limit: 0

Voltage Range Limit: [A] LOW ▼    V Limit: 0

Pulse Width: 0    Tx Gate Width:

PRF: 0    Power Limit: 2000

Probe Temp: 0

Beam Width Tables

|  | 0 | 1 | 2 | 3 | 4 | 5 | 6 | 7 |
|---|---|---|---|---|---|---|---|---|
| Image B Model: | 188 | 205 | 210 | 238 | 208 | 273 | 1073 | 1590 |
| Color B Model: | 200 | 300 | 350 | 400 | 400 | 500 | 1000 | 1500 |

Press Ctrl TAB to go to next property page
Press Ctrl Shift TAB to go to the previous property page

[ OK ]  [ Cancel ]  Apply

FIG. 14B

| Model Type | Safety Info | Image IPA Data | Doppler IPA Data | Color IPA Data | Probe Geometry | In |

Probe 770-0011-00—Probe Model Properties

Image IPA Data

Measured at N Volts

| | 5V | 10V | 15V | 20V | 25V | 30V | 35V | 40V | 45V |
|---|---|---|---|---|---|---|---|---|---|
| Image Zone 0 | 1 | 3 | 8 | 14 | 22 | 32 | 42 | 55 | 67 |
| Image Zone 1 | 1 | 5 | 11 | 19 | 30 | 43 | 58 | 78 | 98 |
| Image Zone 2 | 2 | 12 | 29 | 49 | 69 | 84 | 98 | 114 | 127 |
| Image Zone 3 | 2 | 13 | 32 | 53 | 77 | 93 | 104 | 116 | 125 |
| Image Zone 4 | 3 | 18 | 44 | 65 | 87 | 103 | 121 | 124 | 138 |
| Image Zone 5 | 3 | 15 | 30 | 41 | 53 | 62 | 69 | 76 | 85 |
| Image Zone 6 | 1 | 4 | 9 | 17 | 24 | 31 | 38 | 45 | 51 |
| Image Zone 7 | 1 | 3 | 7 | 13 | 21 | 28 | 35 | 43 | 49 |

Press Ctrl TAB to go to the next property page
Press Ctrl Shift TAB to go to previous property page OK | Cancel | Apply

Probe 770-0011-00- Probe Specifics Properties

Probe Specifics1 | Probe Specifics2 | Image FOV Data1 | Image FOV Data2 | Doppler FOV Data1

— Imaging Static —
Grey Map [0-8]: 6
REP Edge: Level 1
Ventry: OFF

— Doppler Static —
PW Doppler Control: ON
Color Doppler Control: ON
Gate Width [0.1mm]: 60
Gate Depth [0.1mm]: 740
Line Position: 64
Audio Volume: 45
Single Element: 0
Wall [thump] Freq.: 50Hz — FOV Settings —
Active FOV [0-4]: 
FOV Max Index: 2
Copy FOV to FOV: 0

OK  Cancel  Apply

Press Ctrl TAB to go to the next property page
Press Ctrl Shift TAB to go to the previous property page

FIG. 15A

Probe 770-0011-00 - Probe Specifics Properties

Probe Specifics | Probe Specifics 2 | Image FOV Data 1 | Image FOV Data 2 | Doppler FOV Data 1

General Settings

Lines Element: 2
TX Power: 188
Gain: 85
Frame Average: 3
Focus Delay Ctrl.: 0
Focus Frequency: 3.6 MHz
Sample Freq. Dyst.: 26
X Mirror · right =·: DISTAL
Y Mirror · top =·: NEARFIELD
Zone Def. Index: 0

RFP HP Filter: 3.5 MHz
RFP VID Filter: .75 MHz
RFP LP Filter: 5.0 MHz
REP Log Filter: 0.8 MHz
NTSC Y Size: 380
NTSC X Origin: 55
NTSC Y Origin: 45
PAL Y Size: 430
PAL X Origin: 60
PAL Y Origin: 25

Press Ctrl TAB to go to the next property page
Press Ctrl Shift TAB to go to the previous property page OK | Cancel | Apply

FIG. 15B

| Probe 770-0011-00 - Probe Specifics Properties | | |
|---|---|---|
| Probe Specifics1 | Probe Specifics2 | Image FOVData1 | Image FOVData2 | Doppler FOVData1 | | |

Brk Pt TGC Data
- TGC[0]: 60 ◀▶
- TGC[1]: 80 ◀▶
- TGC[2]: 105 ◀▶
- TGC[3]: 125 ◀▶
- TGC[4]: 145 ◀▶
- TGC[5]: 160 ◀▶

Zone Boundaries
- mm[0][0]: 0
- mm[0][1]: 0
- mm[0][2]: 0
- mm[0][3]: 0
- mm[0][4]: 0
- mm[0][5]: 57
- mm[0][6]: 94
- mm[0][7]: 0

Zone Duration
- mm[0][0]: 0
- mm[0][1]: 0
- mm[0][2]: 0
- mm[0][3]: 75
- mm[0][4]: 0
- mm[0][5]: 55
- mm[0][6]: 88
- mm[0][7]: 0

Press Ctrl TAB to goto the next property page
Press Ctrl Shift TAB to go to the previous property page OK | Cancel | Apply

FIG. 15C

ULTRASOUND SCAN CONVERSION WITH SPATIAL DITHERING

RELATED APPLICATIONS

This is a Continuation-In-Part application of International Application No. PCT/US96/11166, filed on Jun. 28, 1996, which is a Continuation-in-Part application of U.S. Ser. No. 08/599,816, filed on Feb. 12, 1996, now U.S. Pat. No. 5,690,174, which is a Continuation-in-Part of U.S. Ser. No. 08/496,804 now U.S. Pat. No. 5,590,658 and 08/496,805 both filed on Jun. 29, 1995, the entire contents of the above applications are being incorporated herein by reference.

BACKGROUND OF THE INVENTION

Conventional ultrasound imaging systems typically include a hand-held scan head coupled by a cable to a large rack-mounted console processing and display unit. The scan head typically includes an array of ultrasonic transducers which transmit ultrasonic energy into a region being imaged and receive reflected ultrasonic energy returning from the region. The transducers convert the received ultrasonic energy into low-level electrical signals which are transferred over the cable to the processing unit. The processing unit applies appropriate beam forming techniques such as dynamic focusing to combine the signals from the transducers to generate an image of the region of interest.

Typical conventional ultrasound systems include transducer arrays having a plurality, for example 128, of ultrasonic transducers. Each transducer is associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beam forming circuits of the processing circuitry introduce the appropriate delay into each low-level electrical signal from the transducers to dynamically focus the signals such that an accurate image can subsequently be generated.

For phased array or curved linear scan heads, the ultrasound signal is received and digitized in its natural polar $(r,\theta)$ form. For display, this representation is inconvenient, so it is converted into a rectangular $(x,y)$ representation for further processing. The rectangular representation is digitally corrected for the dynamic range and brightness of various displays and hard-copy devices. The data can also be stored and retrieved for redisplay. In making the conversion between polar and rectangular coordinates, the $(x,y)$ values must be computed from the $(r,\theta)$ values because the points on the $(r,\theta)$ array and the rectangular $(x,y)$ grid are not coincident.

In prior scan conversion systems, each point on the $(x,y)$ grid is visited and its value is computed from the values of the two nearest $\theta$ values by linear interpolation or the four nearest neighbors on the $(r,\theta)$ array by bilinear interpolation. This is accomplished by use of a finite state machine to generate the $(x,y)$ traversal pattern, a bidirectional shift register to hold the $(r,\theta)$ data samples in a large number of digital logic and memory units to control the process and ensure that the correct asynchronously received samples of $(r,\theta)$ data arrive for interpolation at the right time for each $(x,y)$ point. This prior implementation can be both inflexible and unnecessarily complex. Despite the extensive control hardware, only a single path through the $(x,y)$ array is possible.

SUMMARY OF THE INVENTION

In a preferred embodiment of the invention, scan data is directed into a computer after beamforming and scan conversion is performed to convert the scan data into a display format. In a preferred embodiment, scan conversion can be performed entirely using a software module on a personal computer. Alternatively a board with additional hardware can be inserted to provide selected scan conversion functions or to perform the entire scan conversion process. For many applications, the software system is preferred as additional hardware is minimized so the personal computer can be a small portable platform, such as a laptop or palmtop computer.

Scan conversion is preferably performed using a spatial dithering process described in greater detail below. Spatial dithering simplifies the computational requirements for scan conversion while retaining image resolution and quality. Thus, scan conversion can be performed on a personal computer without the need for more complex interpolation techniques and still provide conversion at frame rates suitable for real time ultrasound imaging.

Preferably, the scan conversion procedure includes an input array, a remap array, and an output array. The remap array is an array of indices or pointers, which is the size of the output image used to determine where to get each pixel from the input array. The numbers in each position in the remap array indicate where in the input data to take each pixel will go into the output array in the same position. Thus, the remap array and output array can be thought of as having the same geometry while the input array and output array have the same type of data, i.e., actual image data.

The input array has new data for each ultrasound frame, which means that it processes the data and puts the data in the output array on every frame. In accordance with a preferred embodiment of the invention, there is a new ultrasound frame approximately every $\frac{1}{30}$ second. Consequently, the remap array data can be generated relatively slowly (but still well under about one second) as long as the routine operation of computing a new output image from a new input data set is performed at the frame rate of approximately 30 frames per second. This allows a general purpose personal computer to perform the task of generating the data for the remap array without compromising performance, but also without having to dedicate additional hardware to the task. In a computing system having a digital signal processor (DSP), the DSP can perform the computations of the remap array.

Alternatively, certain scan conversion functions can be performed by hardware inserted into the personal computer on a circuit board. This board or a card can be inserted and used as an interface to deliver data in the proper form to the PC bus controller.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a block diagram of a conventional imaging array as used in an ultrasound imaging system.

FIG. 3 is a schematic pictorial view of a preferred embodiment of the ultrasound imaging system of the present invention.

FIGS. 14A–14D illustrate display boxes for entering system information.

FIGS. 15A–15C illustrates additional dialog boxes for entering probe or FOV data.

DETAILED DESCRIPTION OF THE INVENTION

Figure 2C:
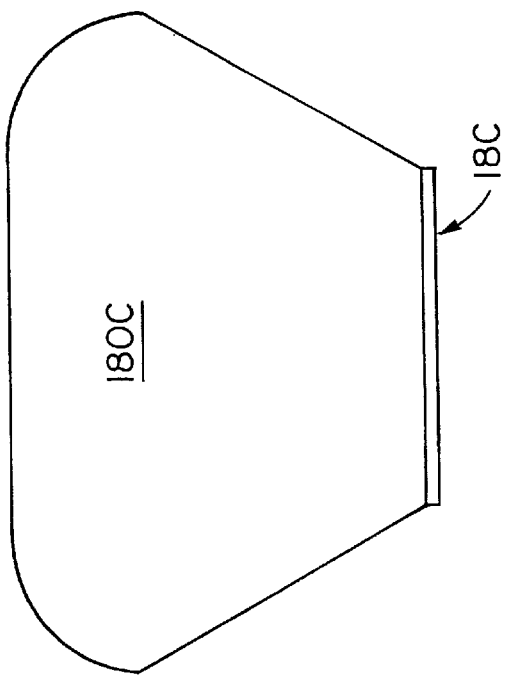
FIG. 2C is a schematic illustration of the relationship between a linear ultrasound transducer array and a trapezoidal scan region in accordance with the present invention.

A schematic block diagram of an imaging array 18 of N piezoelectric ultrasonic transducers 18(1)-18(N) as used in an ultrasound imaging system is shown in FIG. 1. The array of piezoelectric transducer elements 18(1)-18(N) generate acoustic pulses which propagate into the image target (typically a region of human tissue) or transmitting media with a narrow beam 180. The pulses propagate as a spherical wave 185 with a roughly constant velocity. Acoustic echoes in the form of returning signals from image points $I_p$ or reflectors are detected by the same array 18 of transducer elements, or another receiving array and can be displayed in a fashion to indicate the location of the reflecting structure.

The acoustic echo from the image point $I_p$ in the transmitting media reaches each transducer element 18(1)-18(N) of the receiving array after various propagation times. The propagation time for each transducer element is different and depends on the distance between each transducer element and the image point $I_p$. This holds true for typical ultrasound transmitting media, i.e. soft bodily tissue, where the velocity of sound is at least relatively constant. Thereafter, the received information is displayed in a manner to indicate the location of the reflecting structure.

In two-dimensional B-mode scanning, the pulses can be transmitted along a number of lines-of-sight as shown in FIG. 1. If the echoes are sampled and their amplitudes are coded as brightness, a grey scale image can be displayed on a cathode ray tube (CRT) or monitor. An image typically contains 128 such scanned lines at 0.75° angular spacing, forming a 90° sector image. Because the velocity of sound in water is $1.54 \times 10^5$ cm/sec, the round-trip time to a depth of 16 cm will be 208 µs. Thus, the total time required to acquire data along 128 lines of sight (for one image) is 26.6 ms. If other signal processors in the system are fast enough to keep up with this data acquisition rate, two-dimensional images can be produced at rates corresponding to standard television video. For example, if the ultrasound imager is used to view reflected or back scattered sound waves through the chest wall between a pair of ribs, the heart pumping can be imaged in real time.

The ultrasonic transmitter is typically a linear array of piezoelectric transducers 18(1)-18(N) (typically spaced half-wavelength apart) for steered arrays whose elevation pattern is fixed and whose azimuth pattern is controlled primarily by delay steering. The radiating (azimuth) beam pattern of a conventional array is controlled primarily by applying delayed transmitting pulses to each transducer element 18(1)-18(N) in such a manner that the energy from all the transmitters summed together at the image point $I_p$ produces a desired beam shape. Therefore, a time delay circuit is needed in association with each transducer element 18(1)-18(N) for producing the desired transmitted radiation pattern along the predetermined direction.

As previously described, the same array 18 of transducer elements 18(1)-18(N) can be used for receiving the return signals. The reflected or echoed beam energy waveform originating at the image point reaches each transducer element after a time delay equal to the distance from the image point to the transducer element divided by the assumed constant speed of the propagation of waves in the media. Similar to the transmitting mode, this time delay is different for each transducer element. At each receiving transducer element, these differences in path length should be compensated for by focusing the reflected energy at each receiver from the particular image point for any given depth. The delay at each receiving element is a function of the distance measured from the element to the center of the array and the viewing angular direction measured normal to the array.

The beam forming and focusing operations involve forming a sum of the scattered waveforms as observed by all the transducers, but in this sum, the waveforms must be differentially delayed so they will all arrive in phase and properly weighted in the summation. Hence, a beam forming circuit is required which can apply a different delay on each channel, and vary that delay with time. Along a given direction, as echoes return from deeper tissue, the receiving array varies its focus continually with depth. This process is known as dynamic focusing.

After the received beam is formed, it is digitized in a conventional manner. The digital representation of each received pulse is a time sequence corresponding to a backscattering cross section of ultrasonic energy returning from a field point as a function of range at the azimuth formed by the beam. Successive pulses are pointed in different directions, covering a field of view from −45° to +45°. In some systems, time averaging of data from successive observations of the same point (referred to as persistence weighting) is used to improve image quality.

Figure 2D:
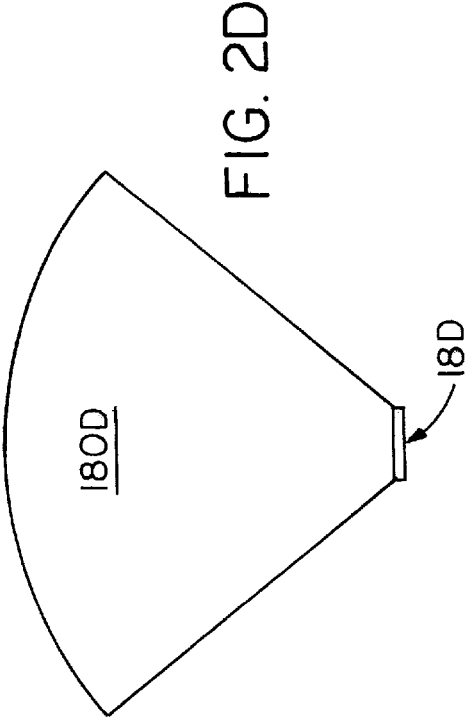
FIG. 2D is a schematic illustration of a phased array scan region.
Figure 2A:
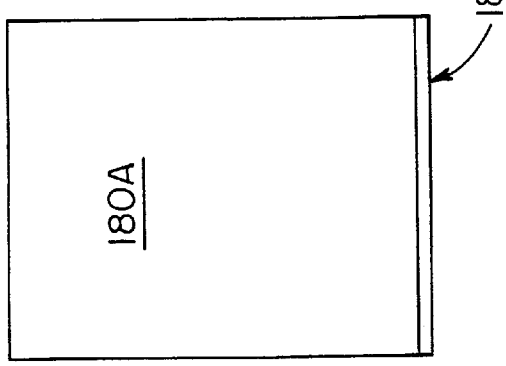
FIG. 2A is a schematic illustration of the relationship between a linear ultrasound transducer array and a rectangular scan region in accordance with the present invention.

FIGS. 2A–2D are schematic diagrams illustrating the relationship between the various transducer array configurations used in the present invention and their corresponding scan image regions. FIG. 2A shows a linear array 18A which produces a rectangular scanning image region 180A. Such an array typically includes 128 transducers.

Figure 2B:
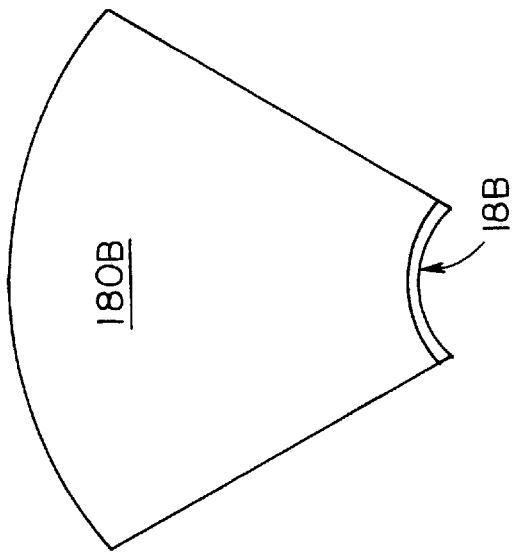
FIG. 2B is a schematic illustration of the relationship between a curved linear ultrasound transducer array and a curved scan region in accordance with the present invention.

FIG. 2B is a schematic diagram showing the relationship between a curved linear transducer array 18B and the resulting sectional curved image scan region 180B. Once again, the array 18B typically includes 128 adjacent transducers.

FIG. 2C shows the relationship between a linear transducer array 18C and a trapezoidal image region 180C. In this embodiment, the array 18C is typically formed from 192 adjacent transducers, instead of 128. The linear array is used to produce the trapezoidal scan region 180C by combining linear scanning as shown in FIG. 2A with phased array scanning. In one embodiment, the 64 transducers on opposite ends of the array 18C are used in a phased array configuration to achieve the curved angular portions of the region 180C at its ends. The middle 64 transducers are used in the linear scanning mode to complete the rectangular portion of the region 180C. Thus, the trapezoidal region 180C is achieved using a sub-aperture scanning approach in which only 64 transducers are active at any one time. In one embodiment, adjacent groups of 64 transducers are activated alternately. That is, first, transducers 1–64 become active. Next, transducers 64–128 become active. In the next step, transducers 2–65 are activated, and then transducers 65–129 are activated. This pattern continues until transducers 128–192 are activated. Next, the scanning process begins over again at transducers 1–64.

FIG. 2D shows a short linear array of transducers 18D used to perform phased array imaging in accordance with the invention. The linear array 18D is used via phased array beam steering processing to produce an angular slice region 180D.

FIG. 3 is a schematic pictorial view of an ultrasound imaging system 10 of the present invention. The system includes a hand-held scan head 12 coupled to a portable data processing and display unit 14 which can be a laptop computer. Alternatively, the data processing and display unit 14 can include a personal computer or other computer interfaced to a CRT for providing display of ultrasound images. The data processor display unit 14 can also be a small, lightweight, single-piece unit small enough to be hand-held or worn or carried by the user. Although FIG. 3 shows an external scan head, the scan head of the invention can also be an internal scan head adapted to be inserted through a lumen into the body for internal imaging. For example, the head can be a transesophogeal probe used for cardiac imaging.

The scan head 12 is connected to the data processor 14 by a cable 16. In an alternative embodiment, the system 10 includes an interface unit 13 (shown in phantom) coupled between the scan head 12 and the data processing and display unit 14. The interface unit 13 preferably contains controller and processing circuitry including a digital signal processor (DSP). The interface unit 13 can perform required signal processing tasks and can provide signal outputs to the data processing unit 14 and/or scan head 12. For user with a palmtop computer, the interface unit 13 is preferably an internal card or chip set. When used with a desktop or laptop computer, the interface unit 13 can instead be an external device.

The hand-held housing 12 includes a transducer section 15A and a handle section 15B. The transducer section 15A is maintained at a temperature below 41° C. so that the portion of the housing that is in contact with the skin of the patient does not exceed this temperature. The handle section 15B does not exceed a second higher temperature preferably 50° C.

Figure 4A:
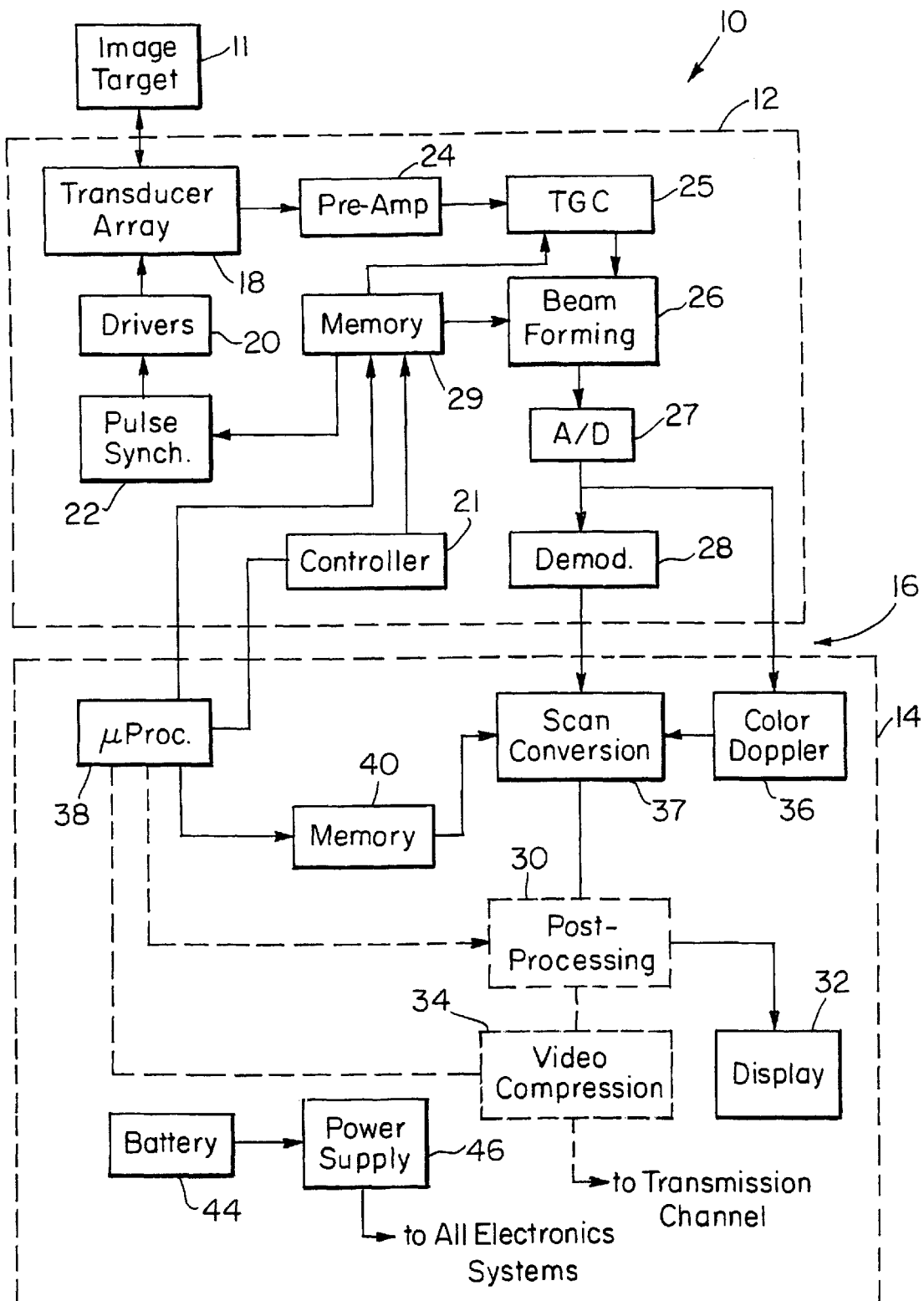
FIG. 4A is a schematic functional block diagram of a preferred embodiment of the ultrasound imaging system of the invention.

FIG. 4A is a schematic functional block diagram of one embodiment of the ultrasound imaging system 10 of the invention. As shown, the scan head 12 includes an ultrasonic transducer array 18 which transmits ultrasonic signals into a region of interest or image target 11, such as a region of human tissue, and receives reflected ultrasonic signals returning from the image target. The scan head 12 also includes transducer driver circuitry 20 and pulse synchronization circuitry 22. The pulse synchronizer 22 forwards a series of precisely timed and delayed pulses to high voltage driver circuits in the drivers 20. As each pulse is received by the drivers 20, the high-voltage driver circuits are activated to forward a high-voltage drive signal to each transducer in the transducer array 18 to activate the transducer to transmit an ultrasonic signal into the image target 11.

Ultrasonic echoes reflected by the image target 11 are detected by the ultrasonic transducers in the array 18. Each transducer converts the received ultrasonic signal into a representative electrical signal which is forwarded to preamplification circuits 24 and time-varying gain control (TGC) circuitry 25. The preamp circuitry 24 sets the level of the electrical signals from the transducer array 18 at a level suitable for subsequent processing, and the TGC circuitry 25 is used to compensate for attenuation of the sound pulse as it penetrates through human tissue and also drives the beam forming circuits 26 (described below) to produce a line image. The conditioned electrical signals are forwarded to the beam forming circuitry 26 which introduces appropriate differential delay into each of the received signals to dynamically focus the signals such that an accurate image can be created. Further details of the beam forming circuitry 26 and the delay circuits used to introduce differential delay into received signals and the pulses generated by the pulse synchronizer 22 are described in the incorporated International Application PCT/US96/11166.

In one preferred embodiment, the dynamically focused and summed signal is forwarded to an A/D converter 27 which digitizes the summed signal. Digital signal data is then forwarded from the A/D 27 over the cable 16 to a color doppler processing circuit 36. It should be noted that the A/D converter 27 is not used in an alternative embodiment in which the analog summed signal is sent directly over the system cable 16. The digital signal is also demodulated in a demodulation circuit 28 and forwarded to a scan conversion circuit 37 in the data processor and display unit 14.

As also shown a scan head memory 29 stores data from a controller 21 and the data processing and display unit 14. The scan head memory 29 provides stored data to the pulse synchronize 22, the TGC 25 and the beam former 26.

The scan conversion circuitry 37 converts the digitized signal data from the beam forming circuitry 26 from polar coordinates (r,θ) to rectangular coordinates (x,y). After the conversion, the rectangular coordinate data can be forwarded to an optional post signal processing stage 30 where it is formatted for display on the display 32 or for compression in a video compression circuit 34. The post processing 30 can also be performed using the scan conversion software described hereinafter.

Digital signal data from the A/D connector 27 is received by a pulsed or continuous Doppler processor 36 in the data processor unit 14. The pulsed or continuous Doppler processor 36 generates data used to image moving target tissue 11 such as flowing blood. In a preferred embodiment, with pulsed Doppler processing, a color flow map is generated. The pulsed Doppler processor 36 forwards its processed data to the scan conversion circuitry 28 where the polar coordinates of the data are translated to rectangular coordinates suitable for display or video compression.

A control circuit, preferably in the form of a microprocessor 38 inside of a personal computer (e.g., desktop, laptop, palmtop), controls the high-level operation of the ultrasound imaging system 10. The microprocessor 38 or a DSP initializes delay and scan conversion memory. The control circuit 38 controls the differential delays introduced in both the pulsed synchronizer 22 and the beam forming circuitry 26 via the scan head memory 27.

The microprocessor 38 also controls a memory 40 which stores data used by the scan conversion circuitry 28. It will be understood that the memory 40 can be a single memory or can be multiple memory circuits. The microprocessor 38 also interfaces with the post signal processing circuitry 30 and the video compression circuitry 34 to control their individual functions. The video compression circuitry 34 compresses data to permit transmission of the image data to remote stations for display and analysis via a transmission channel. The transmission channel can be a modem or wireless cellular communication channel or other known communication method.

The portable ultrasound imaging system 10 of the invention can preferably be powered by a battery 44. The raw battery voltage out of the battery 44 drives a regulated power supply 46 which provides regulated power to all of the subsystems in the imaging system 10 including those subsystems located in the scan head 12. Thus, power to the scan head can be provided from the data processing and display unit 14 over the cable 16.

Figure 4B:
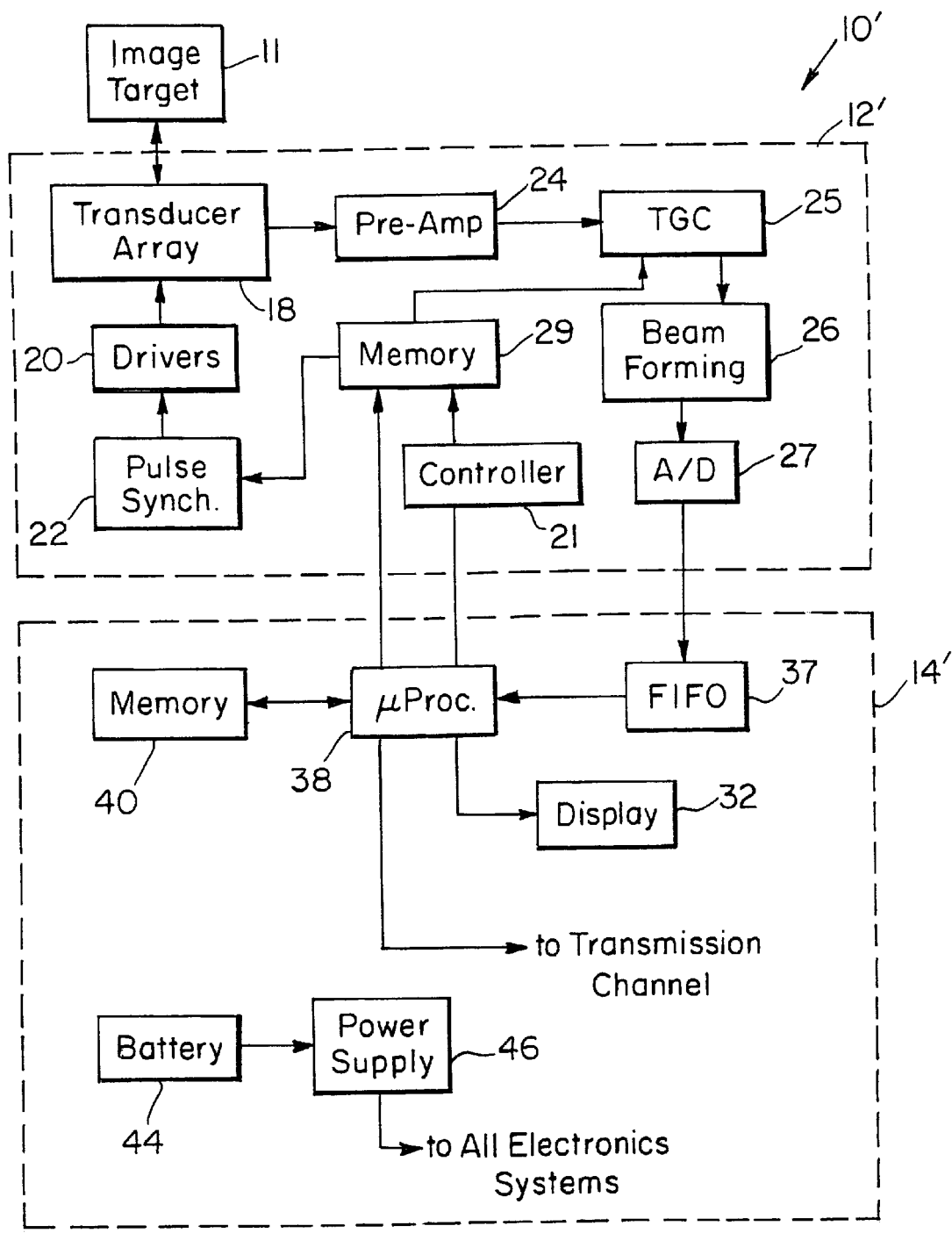
FIG. 4B is a schematic functional block diagram of an alternative preferred embodiment of the ultrasound imaging system of the invention.

FIG. 4B is a schematic functional block diagram of an alternative preferred embodiment of the ultrasound imaging system of the invention. In a modified scan head 12', demodulation circuitry is replaced by software executed by the microprocessor 38 in a modified data processing and display unit 14'. In particular, the digital data stream from the A/D converter 27 is buffered by a FIFO memory 37. The microprocessor executes software instruction to demodulate, perform scan conversion, color doppler processing, post signal processing and video compression. Thus many hardware functions of FIG. 4A are replaced by software stored in memory 40 in FIG. 4B, reducing hardware size and weight requirements for the system 10'.

Figure 5A:
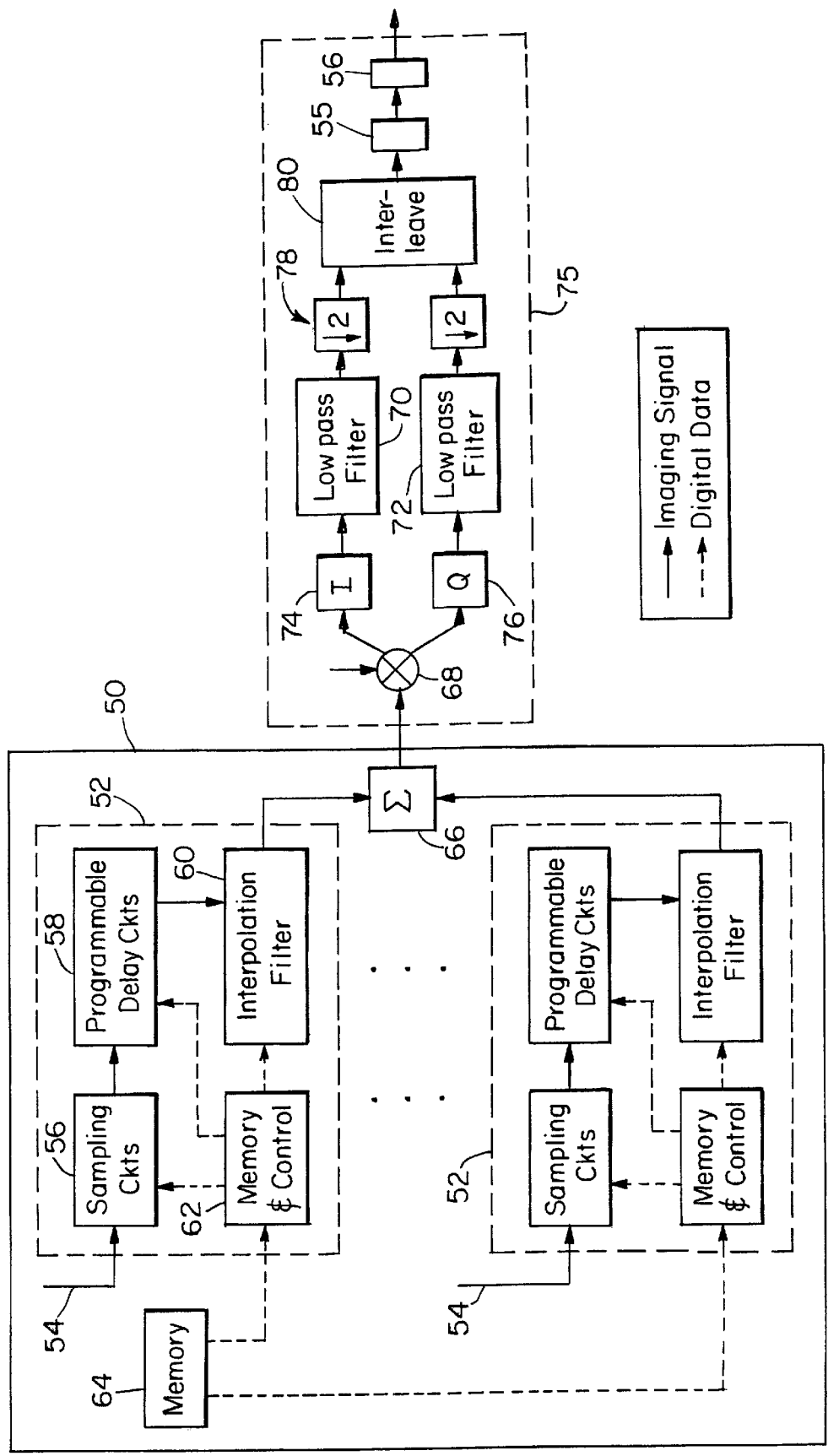
FIG. 5A is a schematic diagram of a beamforming and filtering circuit in accordance with the invention.
Figure 5B:
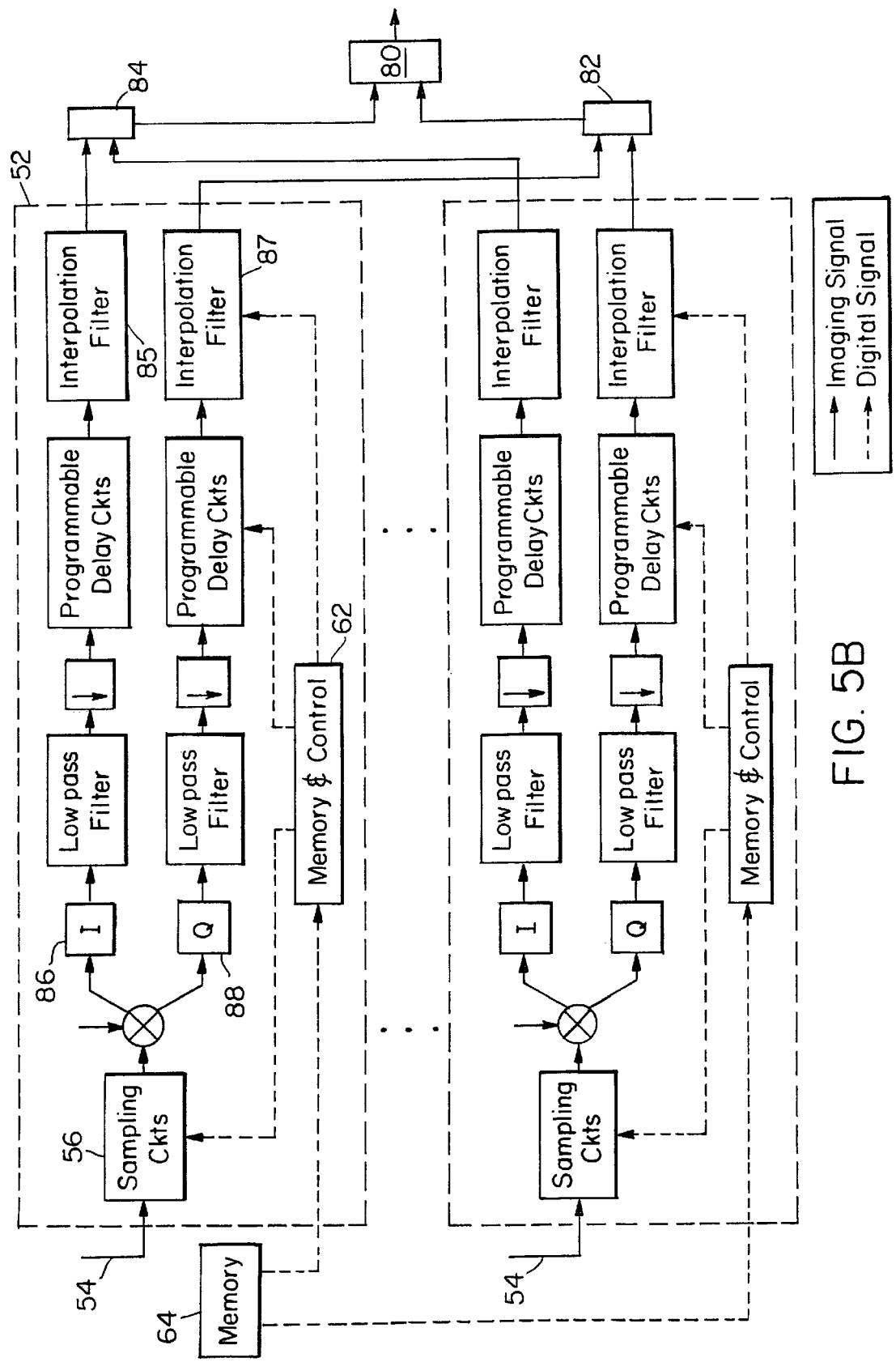
FIG. 5B is a schematic diagram of another preferred embodiment of a beamforming and filtering circuit in accordance with the invention.
Figure 5C:
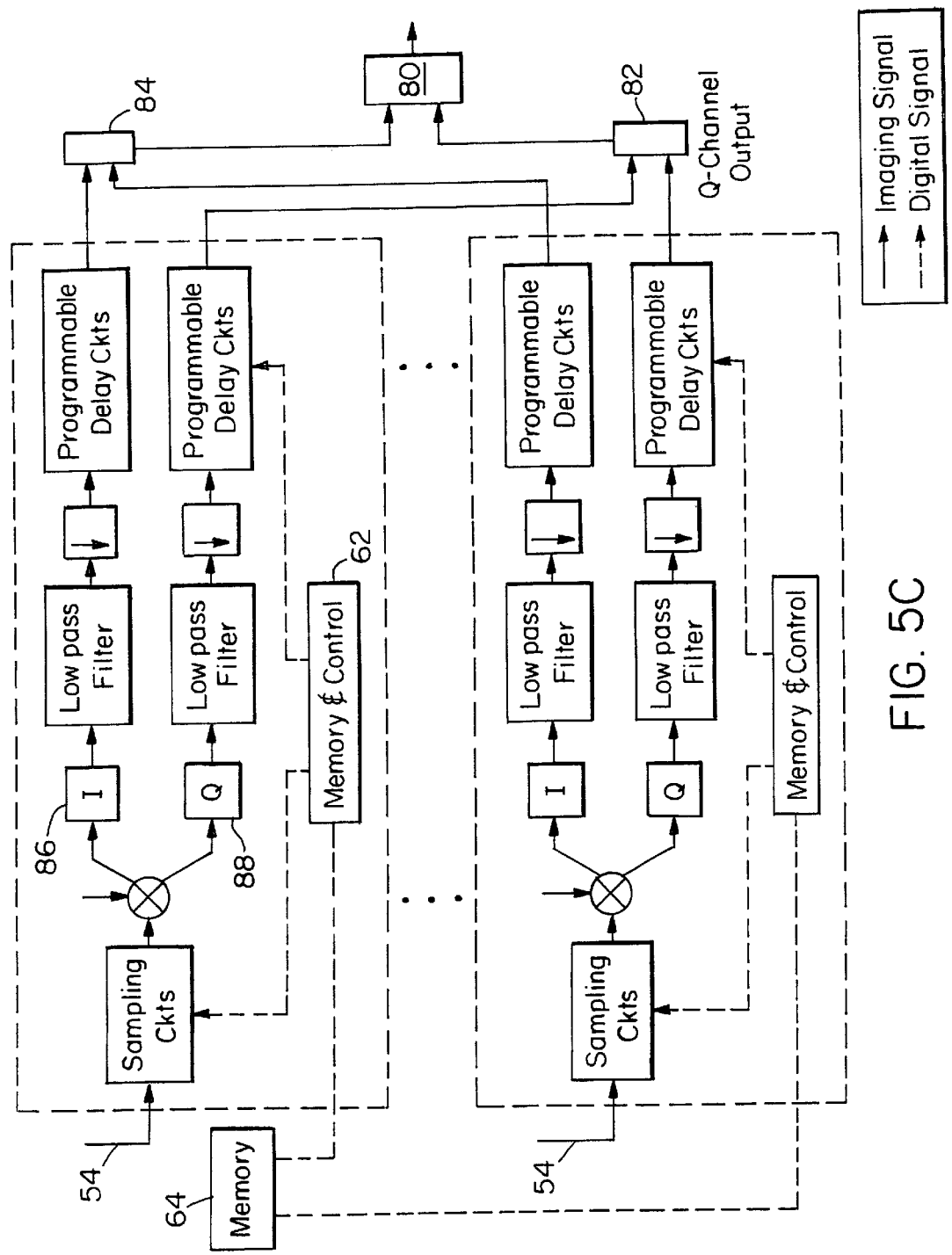
FIG. 5C is a schematic diagram of another preferred embodiment of a beamforming and filtering circuit in accordance with the invention.

Additional preferred embodiments for beam forming circuitry of ultrasound systems are depicted in FIGS. 5A, 5B, and 5C. Each of these implementations requires that sampled-analog data be down-converted, or mixed, to a baseband frequency from an intermediate frequency (IF). The down-conversion or mixing is accomplished by first multiplying the sampled data by a complex value (represented by the complex-valued exponential input to the multiplier stage), and then filtering the data to reject images that have been mixed to nearby frequencies. The outputs of this processing are available at a minimum output sample rate and are available for subsequent display or Doppler processing.

In FIG. 5A, a set of sampling circuits 56 is used to capture a data 54 represented by a packets of charge in a CCD-based processing circuit fabricated on an integrated circuit 50. Data are placed in one or more delay lines and output, at appropriate times using memory and control circuitry 62, programmable delay circuits 58, to an optional interpolation filter 60. The interpolation filter can be used to provide refined estimates of the round-trip time of a sound wave and thereby provide better focus of the returned signals from an array of sensors. In FIG. 5A, two processing channels 52, of an array of processors, are depicted. The outputs from the interpolation filters are combined, at an analog summing junction 66, to provide a datum of beamformed output from the array.

Data obtained using an ultrasound transducer resembles the output of a modest-bandwidth signal modulated by the center frequency of the transducer. The center frequency, or characteristic frequency, of the transducer is equivalent to the IF. In a sample-analog system (e.g., using CCDs), $\Omega=2\pi f_I/f_s$, where $f_I$ is the intermediate frequency and $f_s$ is the sampling frequency. The value n corresponds to the sample-sequence number (i.e., n=0,1,2,3,4, ... ). The outputs of the multiplier 68 are termed, in-phase (I) or quadrature (Q) samples. In general, both I and Q values will be non zero. When the IF is chosen to equal the fs/4, however, the multiplier output will only produce either I or Q values in a repeating sequence, I, Q, –I, –Q, I, Q, –I ... In fact, the input data are only scaled by 1 and –1. Thus, if the input data, a, are sequentially sampled at times, a[0], a[1], a[2], a[3], a[4], . . . , a[n], the output data are a[0], j*a[1], –a[2]. –j*a[3], a[4], . . . , a[n], the output data are a[0], j*a[1], –a[2], –j*a[3], a[4], . . .

The I and Q outputs 74, 76 are each low-pass filtered 70, 72 to reject signal images that are mixed into the baseband. The coefficients of the low-pass filters can be designed using a least-mean square (LMS or L2-norm) or Chebyshev (L-infinity norm) criteria. In practice, it is desirable to reduce the number of coefficients necessary to obtain a desired filter characteristic as much as possible.

Figure 5D:
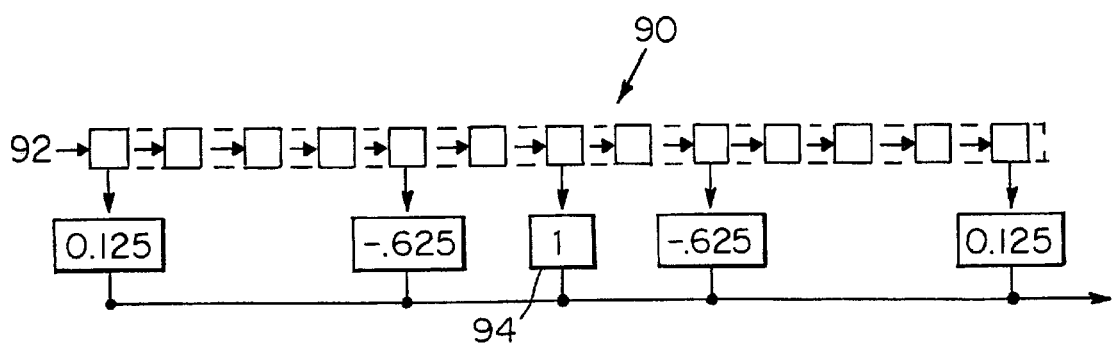
FIG. 5D is a schematic diagram of a low pass filter in accordance with the invention.
Figure 6:
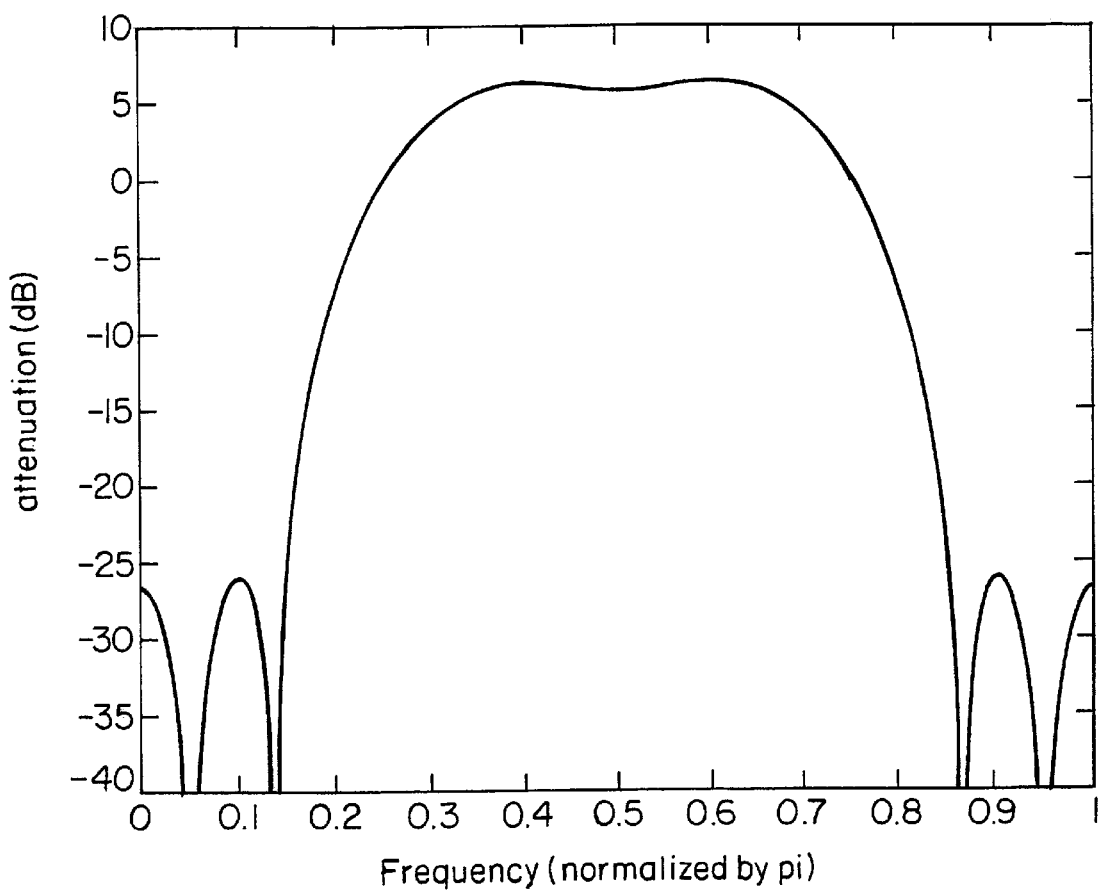
FIG. 6 is a graphical illustration of the passband of a filter in accordance with the invention.

An example of a CCD implementation of a low-pass filter is illustrated in FIG. 5D. The device 90 consists of a 13-state tapped delay line with five fixed-weight multipliers 94 to implement the filter coefficients. As can be seen in the illustration of FIG. 6, the ripple in the passband is under 0.5 dB and the stopband attenuation is less than –30 dB of full scale.

The output of the low-pass filters are then decimated 78 by at least a factor of 2. Decimation greater than 2 may be warranted if the bandwidth of the ultrasound signal is bandlimited to significantly less than half the sampling frequency. For most ultrasound signals, a decimation factor greater than 2 is often used because the signal bandwidth is relatively narrow relative to the sampling frequency.

The order of the decimation and the low-pass filters may be interchanged to reduce the clocking frequency of the low-pass filters. By using a filter bank, the coefficients for the I and Q low-pass filters can be chosen such that each filter only accepts every other datum at its input. This "alternating clock" scheme permits the layout constraints to be relaxed when a decimation rate of 2 is chosen. These constraints can be further relaxed if the decimation factor is greater than 2 (i.e., when the signal bandwidth $\leq \leq f_s/2$).

The down-converted output data are passed on for further processing that may include signal-envelope detection or Doppler processing. For display, the signal envelope (also referred to as the signal magnitude) is computed as the square root of the sum of the squares of the I and Q outputs. For the case when $IF=f_s/4$, that is either I=0 or Q=0, envelope detection becomes trivial. The I and Q data are often the inputs to Doppler processing which also uses the signal envelope to extract information in the positive- and/or negative-frequency sidebands of the signal. In FIG. 5A, only one down-conversion stage is required following the ultrasound beamforming.

In FIG. 5B, a down-conversion stage has been placed in each processing channel 52 following the sampling circuits 56. Here the production of I and Q data 86, 88 is performed exactly as before, however, much sooner in the system. The primary advantage of this approach is that the data rate in each processing channel can be reduced to a minimum, based on the ultrasound signal bandwidth and hence the selection of the low-pass filter and decimation factor. In this implementation, all processing channels 52 will use the same complex-value multipliers and identical coefficients and decimation factors in the filter stage. As in the preceding implementation, complex-valued data are delayed and interpolated to provide beamformed output.

The ultrasound front end depicted in FIG. 5C is nearly identical to that in FIG. 5B. The difference is that the interpolation stage 85, 87 has been removed and replaced by choosing unique values in the complex-valued multipliers to provide a more-precise estimate of the processing-channel delay. This approach has the disadvantage that the output of the multiplier will always exhibit I and Q values that are non zero. This is a consequence of the varying sampling rate around the unit circle, in a complex-plane diagram, of the multiplier input. Thus, this approach can provide a more precise estimate of the sample delay in each channel, but at the expense of producing fully complex-valued data at the output of each processing channel. This modification may require more post-processing for envelope and Doppler detection than that presented in the previous implementations.

A preferred embodiment of a system used to interface between the output of the beamforming or filtering circuit and the computer is to provide a plug in board or card (PCMCIA) for the computer.

Figure 5E:
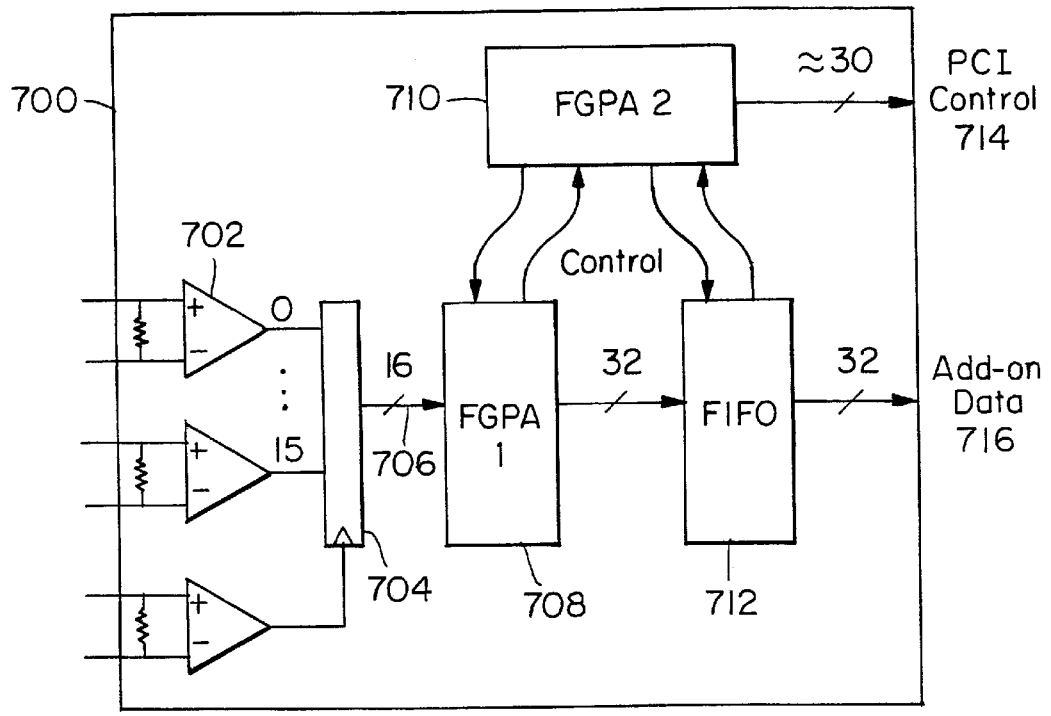
FIG. 5E is an example of an interface circuit board in accordance with the invention.

The board 700 of FIG. 5E illustrates an embodiment in which 16 bits of digital beamformed data are received over the cable from the scanhead by differential receivers 702. A clock signal is also received at registers 704 along with converted differential data. The first gate array 708 converts the 16 bits to 32 bits at half the data rate. The 32 bit data is clocked into the FIFO 712 which outputs add-on data 716. The second gate array 710 has access to all control signals and outputs 714 to the PCI bus controller. This particular example utilizes 16 bits of data, however, this design can also be adapted for 32 bits or more.

Alternatively, a card suitable for insertion in a slot or port of a personal computer, laptop or palmtop computer can also be used. In this embodiment the differential receivers input to registers, which deliver data to the FIFO and then to a bus controller that is located on the card. The output from the controller is connected directly to the PCI bus of the computer. An alternative to the use of differential drivers and receivers to interconnect the scan head to the interface board or card is to utilize the IEEE 1394 standard cable also known as "firewire".

Figure 5F:
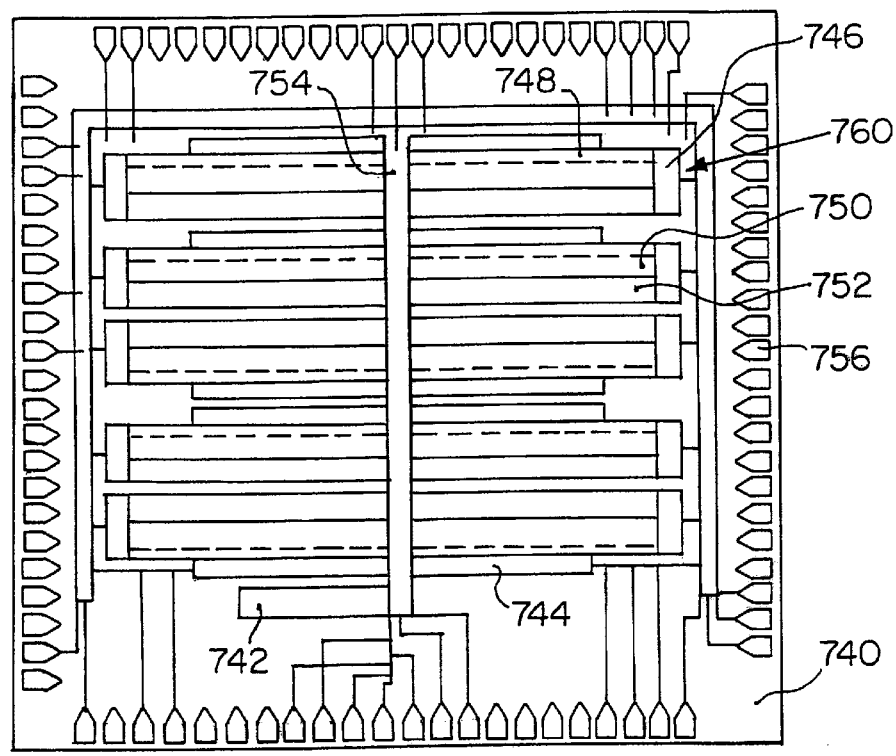
FIG. 5F is a preferred embodiment of an integrated beamforming circuit in accordance with the inventions.

An example of a preferred embodiment of an integrated beamforming circuit 740 is illustrated in FIG. 5F. The circuit 740 includes a timing circuit 742, and 5 delay circuits 760 attached to each side of summing circuit 754. Each circuit 760 includes a sampling circuit 746, a CCD delay line 752, a control and memory circuit 750, a decoder 748, and a clocking driver circuit 744. The circuity is surrounded by contact pads 756 to provide access to the chip circuitry. The integrated circuit is preferably less than 20 square millimeters in area and can be mounted on a single board in the scan head as described in the various embodiments set forth in the above referenced incorporated application. A sixteen, thirty two, or sixty four delay line integrated circuit can also be implemented utilizing a similar structure.

Figure 7A:
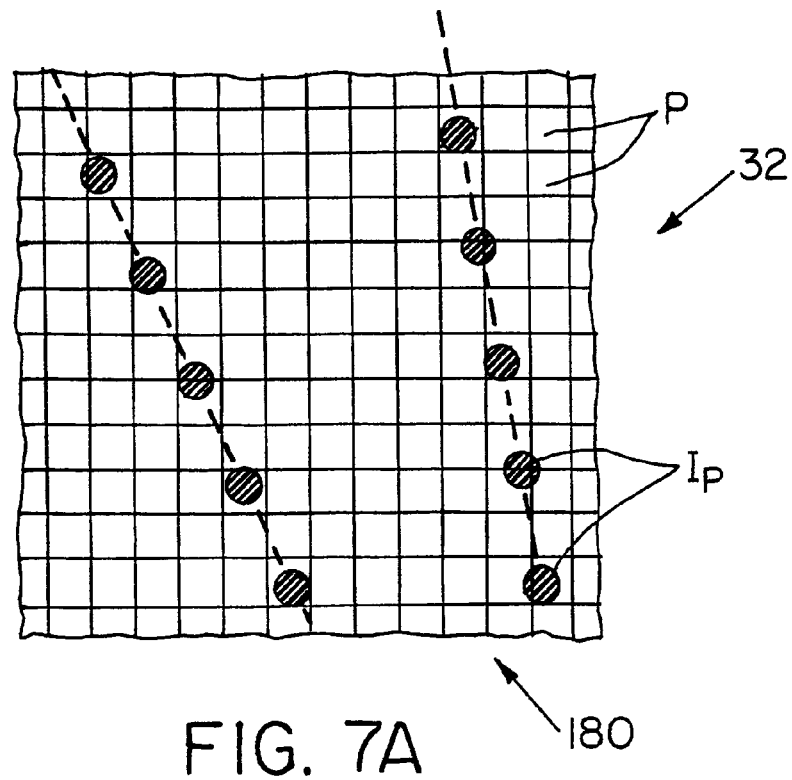
FIG. 7A is a schematic diagram of input points overlayed on a display.

FIG. 7A is a schematic diagram of input points overlayed on a display. As illustrated, input points $I_p$ received from the ultrasound beam 180 do not exactly align with the rectangular arranged pixel points P of a conventional display 32. Because the display 32 can only display pixelized data, the input points $I_p$ must be converted to the rectangular format.

Figure 7B:
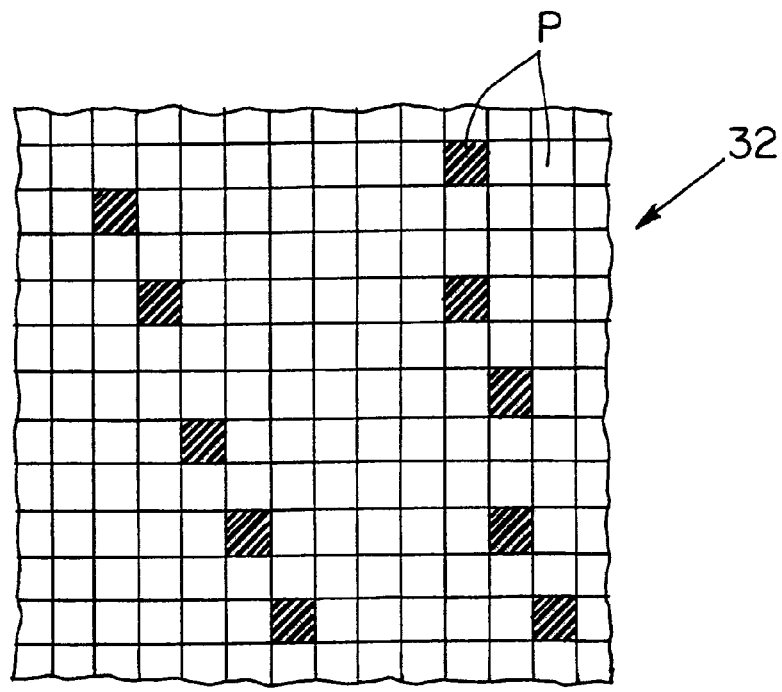
FIG. 7B is a schematic diagram of a display of FIG. 6 having input data converted to pixels.

FIG. 7B is a schematic diagram of a display of FIG. 6 having input data converted to pixels. As illustrated, each image point $I_p$ is assigned to a respective pixel point P on the display 32 to form an image.

One purpose of scan conversion is to perform the coordinate space transformation required for use with scan heads that are not flat linear, such as phased array, trapezoidal or curved linear heads. To do this, data must be read in one order and output data must be written in another order. Many existing systems must generate the transformation sequences on the fly, which reduces the flexibility and makes trapezoidal scan patterns more difficult.

Because scan conversion is reordering the data, it can also be used to rotate, pan and zoom the data. Rotation is useful for viewing the image with the scan head depicted at the top, left, right, or bottom of the image, or an arbitrary angle. Zooming and panning are commonly used to allow various parts of the image to be examined more closely.

In addition to zooming into one area of the object, it is useful to be able to see multiple areas simultaneously in different regions of the screen. Often the entire image is shown on the screen but certain regions are replaced with zoomed-in-views. This feature is usually referred to as "window-in-a-window." Current high-end systems provides this capability for one window, but it is preferred that an imaging system allow any number of zoomed regions, each of which having an arbitrary size and shape.

The use of irregular scan patterns can ease system design and allow greater scan head utilization. In particular, this allows reduction or hiding of dead time associated with imaging deep zones. In the case of deep zone imaging, the beam is transmitted but received at some later time after the wave has had time to travel to the maximum depth and return. More efficient use of the system, and thus a higher frame rate or greater lateral sampling, can be obtained if other zones are illuminated and reconstructed during this dead time. This can cause the scan pattern to become irregular (although fixed and explicitly computed). The flexible scan conversion described below corrects for this automatically.

Figure 8:
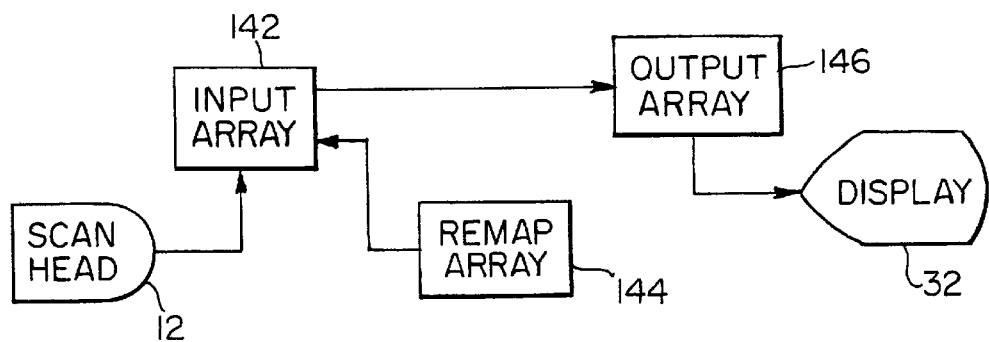
FIG. 8 is a schematic diagram of a preferred embodiment of a general purpose image remapping architecture.

FIG. 8 is a schematic diagram of a preferred embodiment of a general purpose image remapping architecture. In accordance with a preferred embodiment of the invention, data is preferably brought directly into the PC after beamforming and the remainder of the manipulation is performed in software. As such, additional hardware is minimized so the personal computer can be a small portable platform, such as a laptop or palmtop computer.

Preferably, there is an input array 142, a remap array 144 and an output array 146. The remap array 144 is an array of indices or pointers, which is the size of the output image used to determine where to get each pixel from the input array 142. The numbers in each position in the remap array 144 indicate where in the input data to take each pixel which will go into the output array 146 in the same position. Thus, the remap array 144 and output array 196 can be thought of as having the same geometry while the input array 142 and output array 146 have the same type of data, i.e., actual image data.

The input array 142 has new data for each ultrasound frame, which means that it processes the data and puts the data in the output array 146 on every frame. In accordance with the invention, there is a new ultrasound frame at a rate of at least 20 frames per second and preferably approximately every 1/30 second. However, the remap array 144 is only updated when the head type or viewing parameters (i.e., zoom and pan) are updated. Consequently, the remap array 144 data can be generated relatively slowly (but still well under about one second or else it can become cumbersome) as long as the routine operation of computing a new output image from a new input data set is performed at the frame rate of approximately 30 frames per second. This allows a general purpose personal computer to perform the task of generating the data for the remap array 144 without compromising performance, but also without having to dedicate additional hardware to the task. In a computing system having a digital signal processor (DSP), the DSP can perform the computations of the remap array 144.

In a preferred embodiment of the invention, input memory for the input array 142 can be either two banks of Static Random Access Memory (SRAM) or one bank of Video Random Access Memory (VRAM), where the input is serial access and the output is random access. The VRAM bank, however, may be too slow and refresh too costly. The remap memory for the remap array 144 is preferably sequential access memory embodied in VRAM, or Dynamic Random Access Memory (DRAM), although random access SRAM will also work. The output memory for the output array 146 can be either a frame buffer or a First-In First-Out (FIFO) buffer. Basically, the scan conversion is done on demand, on the fly. Scan conversion is preferably performed by software in the PC. If scan conversion is done in hardware, however, the PC is merely storing data, thus reducing system complexity. Thus, an architecture in accordance with the invention is preferably just two random access input buffers, a sequential access remap buffer and small (if any) FIFO or bit of pipelining for the output buffer. This implies the output frame buffer is in PC memory.

In accordance with a preferred embodiment of the invention, a spatial dithering technique employing error diffusion is used in ultrasound scan conversion. Typical dithering is done in the pixel intensity domain. In accordance with the invention, however, dithering is used in ultrasound scan conversion to approximate pixels in the spatial domain and not in the pixel intensity domain. Spatial dithering is used to approximate values that fall between two input data points. This happens because only discrete radii are sampled but pixels on the display screen can fall between two radii and need to be filtered. Spatial dithering must be used to interpolate between longitudinal sample points.

Recall that the remap array 144 stores the mapping of each output point to an input point. The input data points are typically in polar coordinates while the output points are in rectilinear coordinates. Although the remap array 144 merely contains indices into the input array 142, they can be considered to contain radius (r) and angle (θ) values. Ideally, these values have arbitrary precision and do not have to correspond to actual sampled points. Now consider that these arbitrary precision numbers must be converted into integer values. The integer radius values correspond to discrete samples that were taken and are limited by the radial sampling density of the system. The integer angle values correspond to discrete radial lines that were scanned and are thus limited by the number of scan angles. If spatial dithering is applied, these floating point values can be mapped into fixed integer values without having the artifacts that appear with discrete rounding without error diffusion.

Figure 9A:
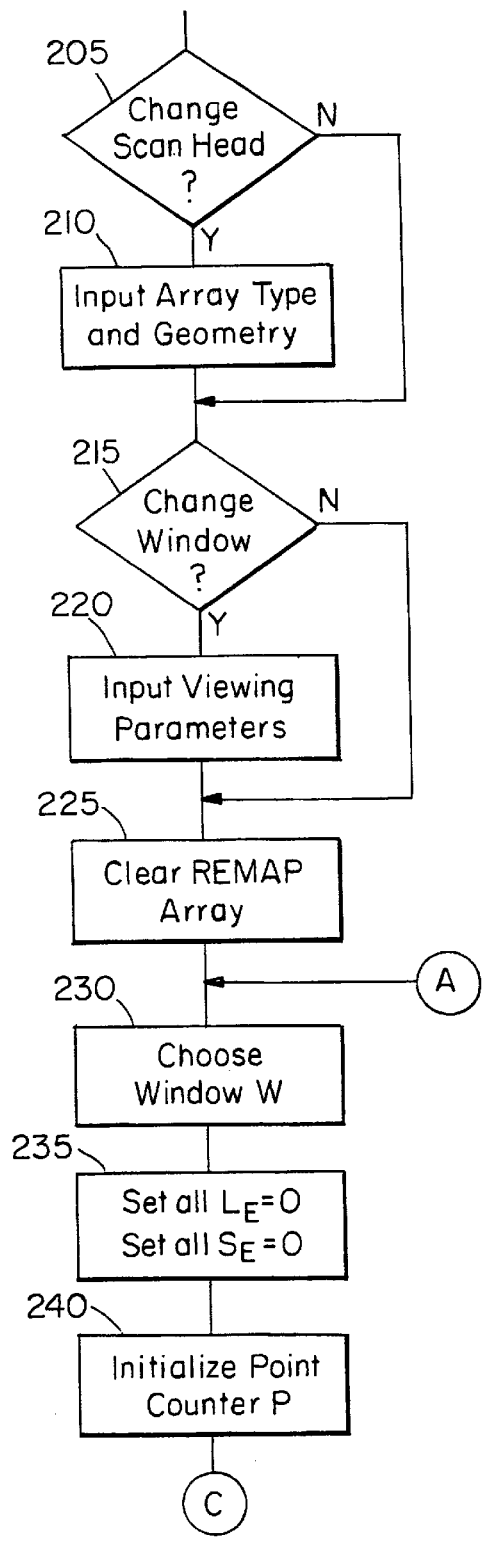
FIGS. 9A–9B are a flow chart illustrating a remap array computation technique in accordance with the invention.
Figure 9B:
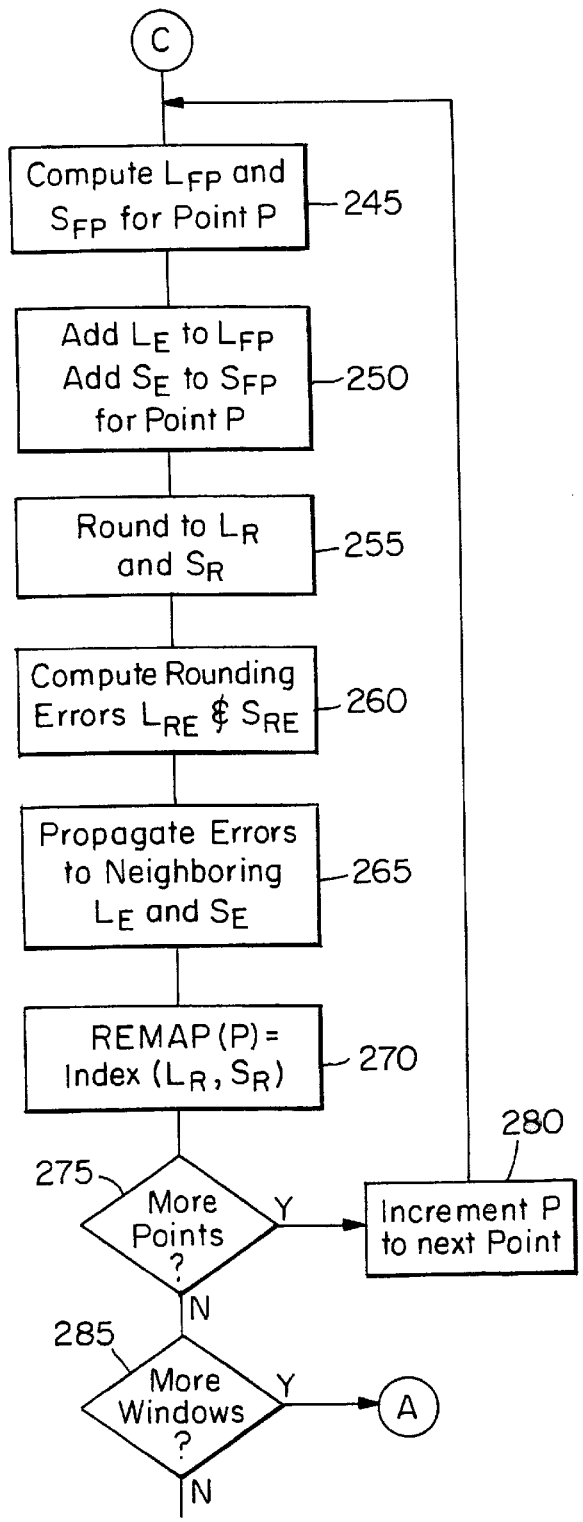

FIGS. 9A–9B are a flow chart illustrating a remap array computation technique in accordance with the invention. At step 205, the scan heads are checked to see if there has been any change. If the scan heads have been changed, processing continues to step 210 where the new head type is configured. After step 210, or if there has been no change in the scan heads (step 205) processing continues to step 215. At step 215, the display window is checked to see if there is any zooming, panning or new window-in-window feature. If so, processing continues to step 220 where the user inputs the new viewing parameters. After step 220, or if there is no window change at step 215, processing continues to step 225 where the remap array is cleared to indicate a new relationship between the input and output arrays.

At step 230, the program chooses a window W to process. At step 235, all line error values $L_E$ and all sample error values $S_E$ are initialized to zero. At step 240, a point counter P is initialized to point to the top left pixel of the window W.

At step 245, the application computes a floating point line number $L_{FP}$ and sample offset $S_{FP}$ for each point in a view V. For a phased array, this would be a radius r and an angle θ. At step 250, any previously propagated error terms $L_E$, $S_E$ (discussed below) are added to the floating point values $L_{FP}$, $S_{FP}$ for the point P. At step 255, floating point terms are rounded to the nearest integer $L_R$, $S_R$, which correspond to actual sampled points. At step 260, the application computes rounding errors as:

$$L_{RE} = L_{FP} - L_R;$$

$$S_{RE} = S_{FP} - S_R.$$

At step 265, the errors are propagated to the pixel points to the right, below left, below, and below right relative to the current point P.

PROPAGATE ERRORS $L_E$ (right)=$L_E$ (right)+$L_{RE}$ * 7/16

$L_E$ (below left)=$L_E$ (below left)+$L_{RE}$ * 3/16

$L_E$ (below)=$L_E$ (below)+$L_{RE}$ * 5/16

$L_E$ (below right)=$L_E$ (below right)+$L_{RE}$ * 1/16

$S_E$ (right)=$S_E$ (right)+$S_{RE}$ * 7/16

$S_E$ (below left)=$S_E$ (below left)+$S_{RE}$ * 3/16

$S_E$ (below)=$S_E$ (below)+$S_{RE}$ * 5/16

$S_E$ (below right)=$S_E$ (below right)+$S_{RE}$ * 1/16

At step 270, the application computes a data index based on a scan data ordered index:

REMAP(P)=Index($L_R$, $S_R$).

At step 275, a check is made to see if there are more points in the window. If there are more points to be processed, the pointer P is incremented to the next point at step 280. Processing then returns to step 245. Once all points in the window have been processed, processing continues to step 285.

At step 285, a check is made to see if there are more windows to be processed. If so, processing returns to step 230. Otherwise, processing is done.

Because the dithering maps one source to each output pixel, the same remapping architecture can be used to make real-time scan conversion possible in software, even on portable computers. Thus, the complicated dithering operation is only performed during initialization or when viewing parameters are changed. However, the benefits of the dithering are present in all the images.

Figure 10:
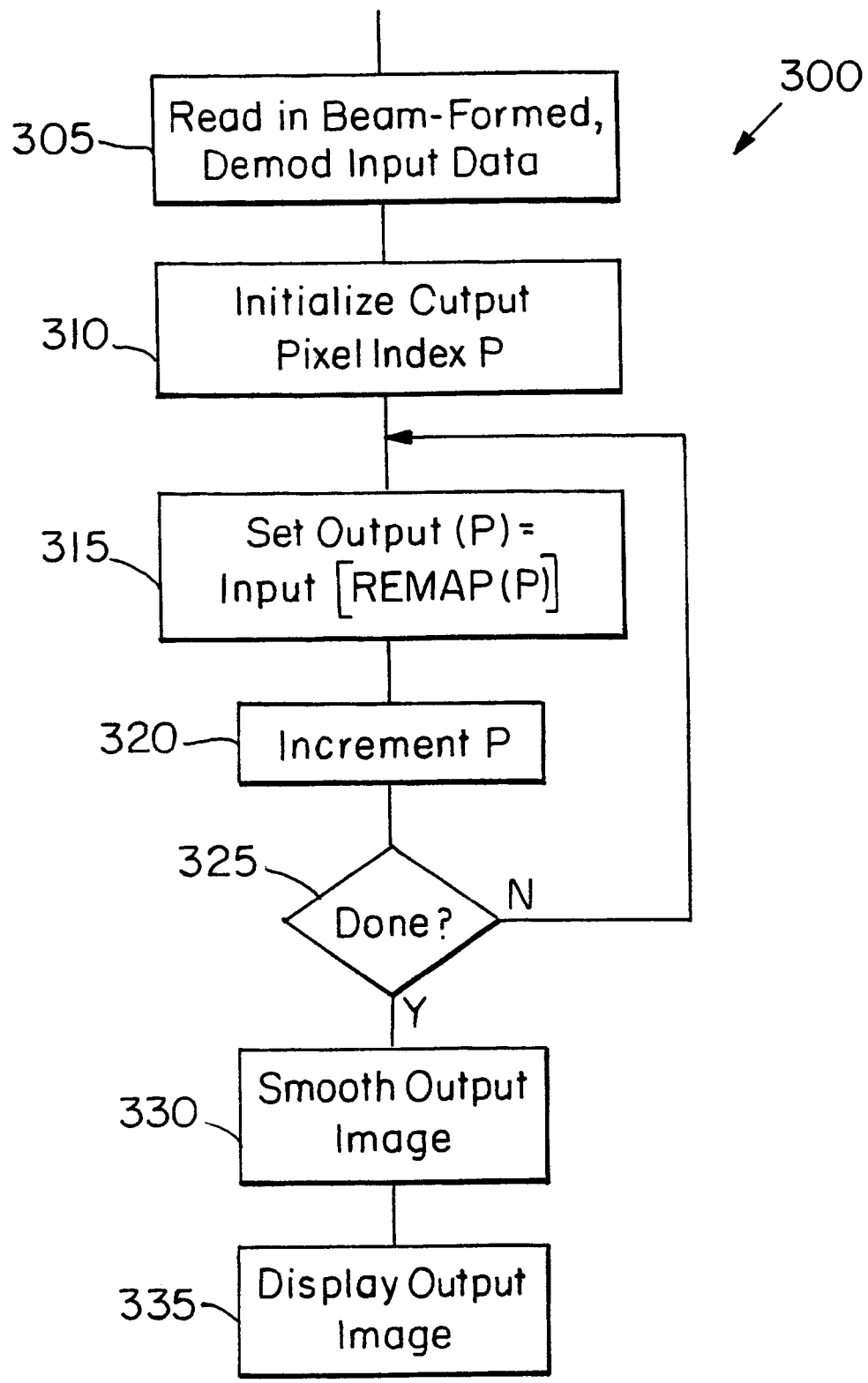
FIG. 10 is a flow chart of an output frame computation engine.

FIG. 10 is a flow chart of an output frame computation engine. At step 305, beamforming, demodulated input data is read into memory. At step 310, the output pixel index P is initialized. At step 315, the output array is set equal to the remapped input array according to the following:

OUTPUT(P)=INPUT(REMAP (P)).

At step 320, the output pixel index P is incremented. At step 325, a check is done on the pixel index P to see if the image has been formed. If not, processing returns to step 315. Once all the pixels in the image have been computed, processing continues to step 330 where the output image is optionally smoothed. Finally, at step 335, the output image is displayed.

Although dithering does remove the mach-banding and moire pattern artifacts which occur with simple rounding, dithering can introduce high-frequency noise. It is this high-frequency noise whose average value allow for the smooth transition effects. To the untrained eye, these artifacts are far less objectionable than those obtained with the simple rounding or nearest-point case, but may be objectionable to ultrasound technicians.

These artifacts can be greatly reduced or potentially eliminated by employing a low-pass spatial filter to smooth the image after the remapping process. The filter can be a box filter or non-symmetrical filters can be matched to a desired input resolution characteristic. Filters can be applied in the rectilinear domain that match the orientation or angle of point coordinates at the particular location.

Basically, it is desirable to have a matched filter whose extent is similar to or proportional to distances between points being dithered. Thus, a high magnification is preferably accompanied by a large filter with much smoothing, whereas in places with a spacing of the sampled radius r or angle (θ) is small (on the order of one pixel), no filtering may be required.

Because the remapping operation is basically two loads and a store, it can be performed using a standard personal computer. The remapping algorithm when encoded in assembly language has been shown to work on a 166 MHZ Pentium-based PC to obtain very-near real-time operation. In addition, the demodulation has been performed on the PC when written in assembly language while still achieving near real-time operation. Text and graphics labels are preferably effected by storing fixed values or colors in the beginning of the input buffer and then mapping to those places where those colors are to be used. If effect, shapes or text are drawn in the remap array, which will open and automatically be overlayed on all of the images at no computational cost.

Figure 11A:
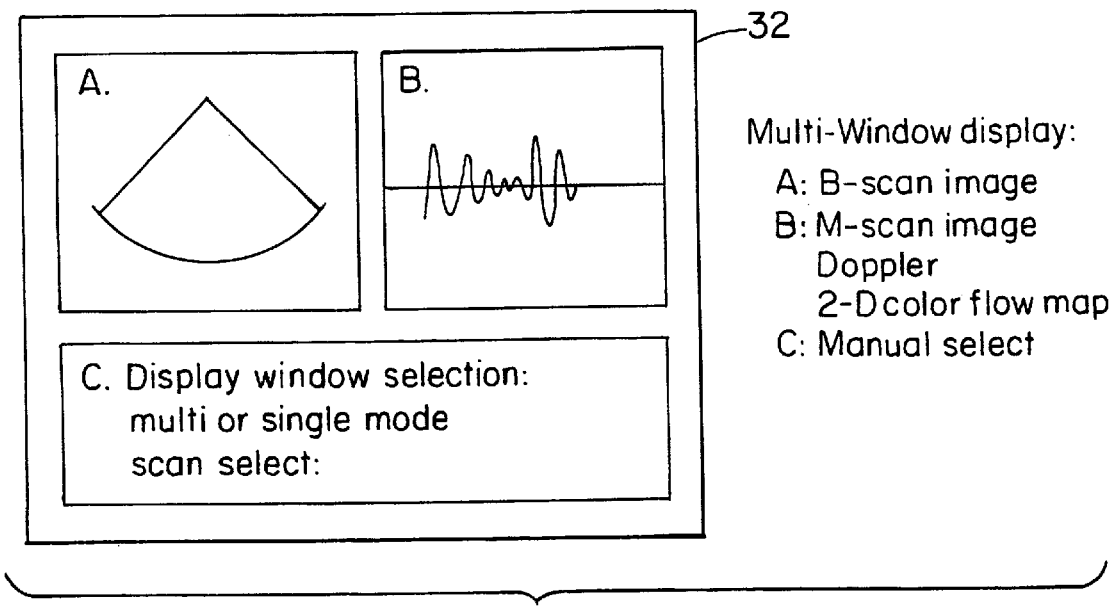
FIGS. 11A–11B are schematic pictorial views of two user-selectable display presentation formats used in the ultrasound imaging system of the invention.
Figure 11B:
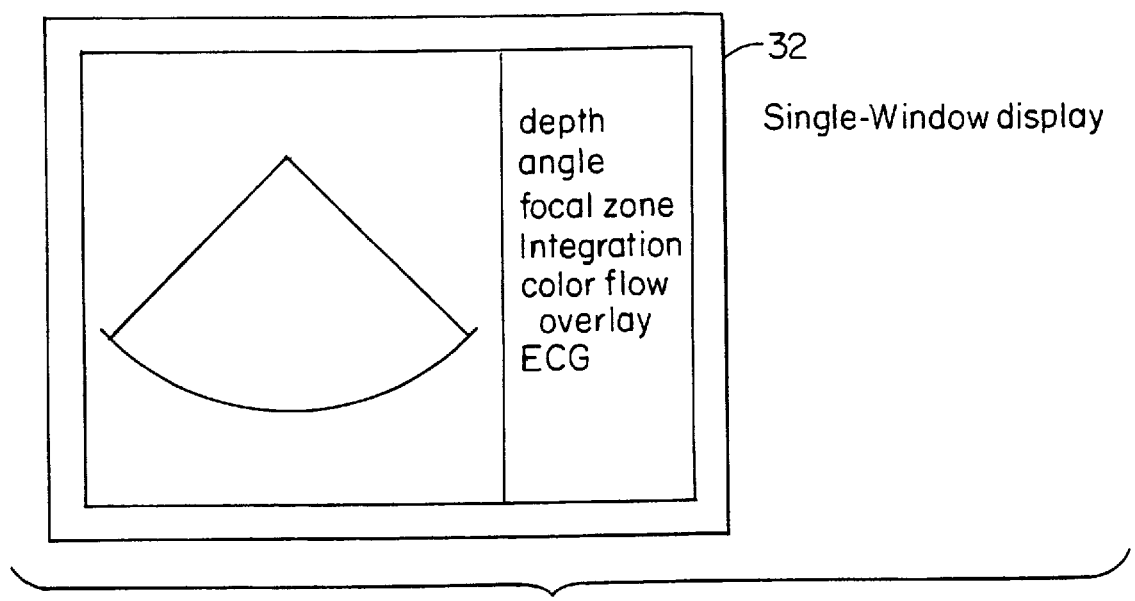

FIGS. 11A–11B are schematic pictorial views of display formats which can be presented on the display 32 of the invention. Rather than displaying a single window of data as is done in prior ultrasound imaging systems, the system of the present invention has multiple window display formats which can be selected by the user. FIG. 11A shows a selectable multi-window display in which three information windows are presented simultaneously on the display. Window A shows the standard B-scan image, while window B shows an M-scan image of a Doppler two-dimensional color flow map. Window C is a user information window which communicates command selections to the user and facilitates the user's manual selections. FIG. 11B is a single-window optional display in which the entire display is used to present only a B-scan image. Optionally, the display can show both the B-mode and color doppler scans simultaneously by overlaying the two displays or by showing them side-by-side using a split screen feature.

Figure 12:
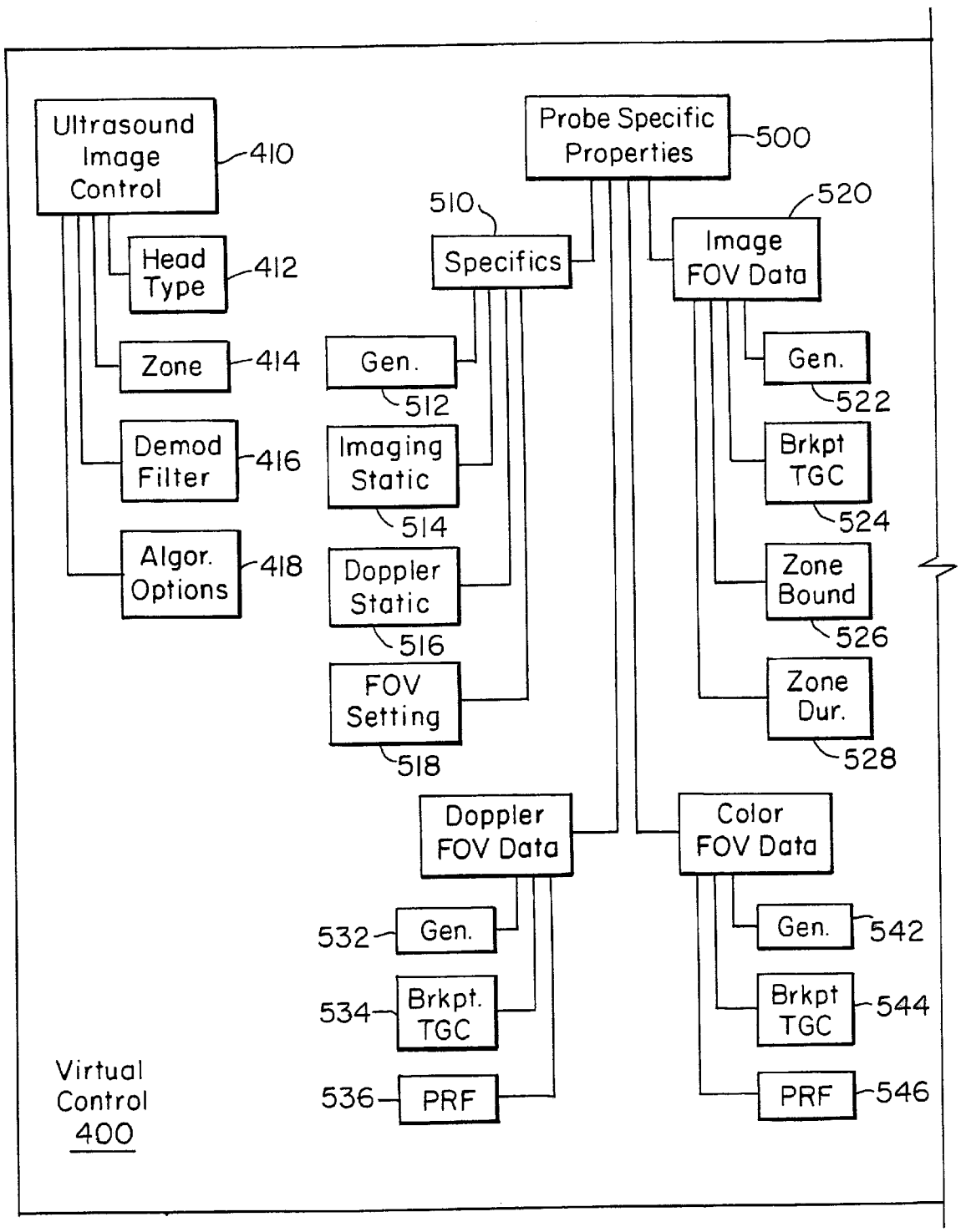
FIG. 12 is a functional block diagram of a preferred graphical user interface.

FIG. 12 is functional block diagram of a preferred graphical user interface. A virtual control 400 includes an ultrasound image control display 410, a probe model properties display 420, and a probe specific properties display 500. The virtual control display 400 is preferably coded as dialog boxes in a Windows environment.

Figure 13:
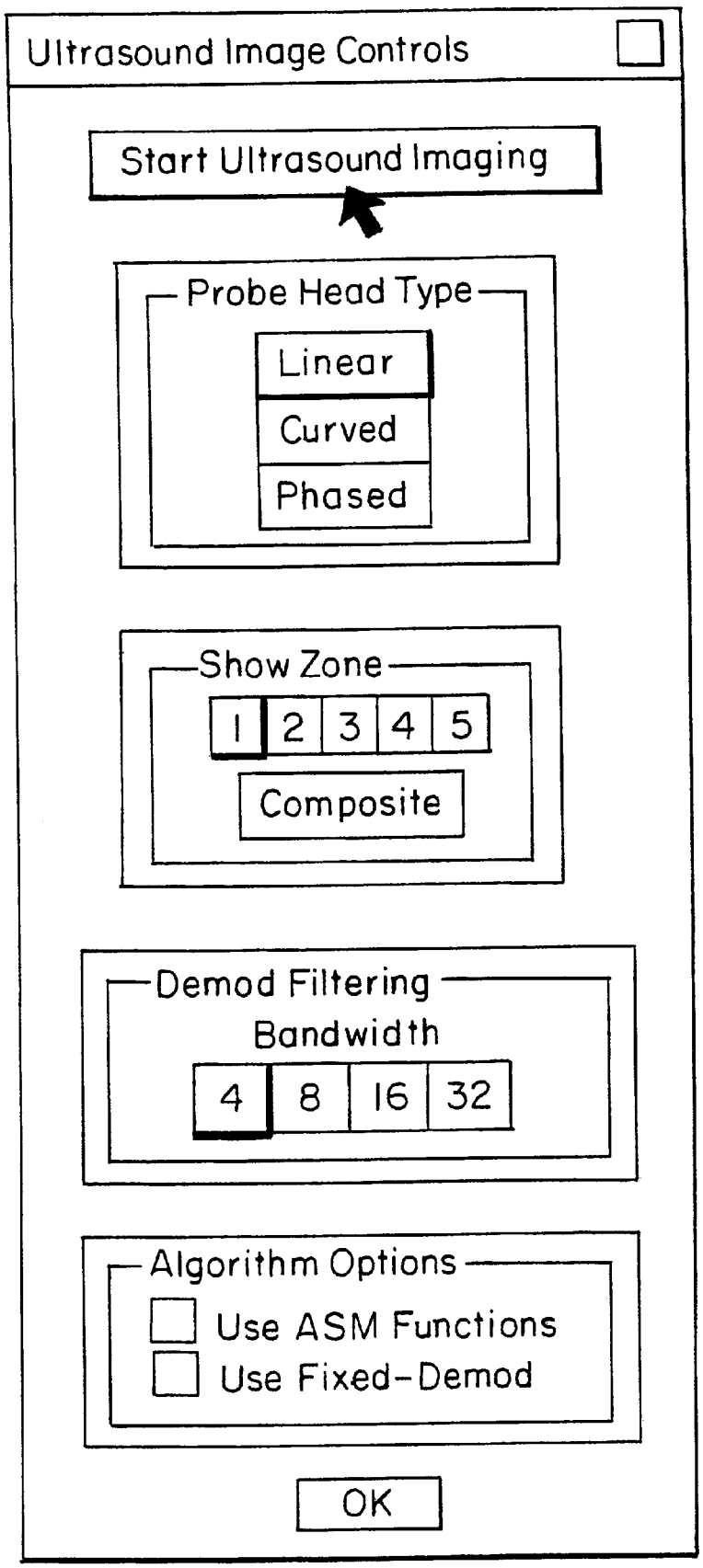
FIG. 13 illustrates a dialog box for ultrasound image control.

FIG. 13 illustrates a dialog box for the ultrasound image control 410. Through the ultrasound image control display 410, the user can select a probe head type 412, a zone display 414, a demodulation filter 416, and an algorithm option 418. The user also can initiate the ultrasound scan through this dialog box.

The probe model properties display 420 includes model type 425, safety information 430, image Integrated Pulse Amplitude (IPA) data 435, doppler IPA data 440, color IPA data 445, probe geometry 450, image zones data 455, doppler zones data 460, color zones data 465, image apodization 470, doppler apodization 475, and color apodization 480. These are preferably encoded as dialog boxes. Through the model-properties dialog box 425, a user can enter general settings for the probe model.

FIG. 14A illustrates a dialog box for entering a viewing probe model properties. Entered parameters are downloaded to the ultrasound probe.

FIG. 14B illustrates a dialog box for entering and viewing safety information 430. As illustrated, a user can enter general settings 432 and beam width table data 434 per governing standards.

FIG. 14C illustrates a dialog box for entering and viewing image IPA data 435. The dialog box displays beamformed output values, listed in volts as a function of image display zones for various drive voltages. Similar dialog boxes are used to enter the doppler and color IPA data 440, 445.

Figure 14D:
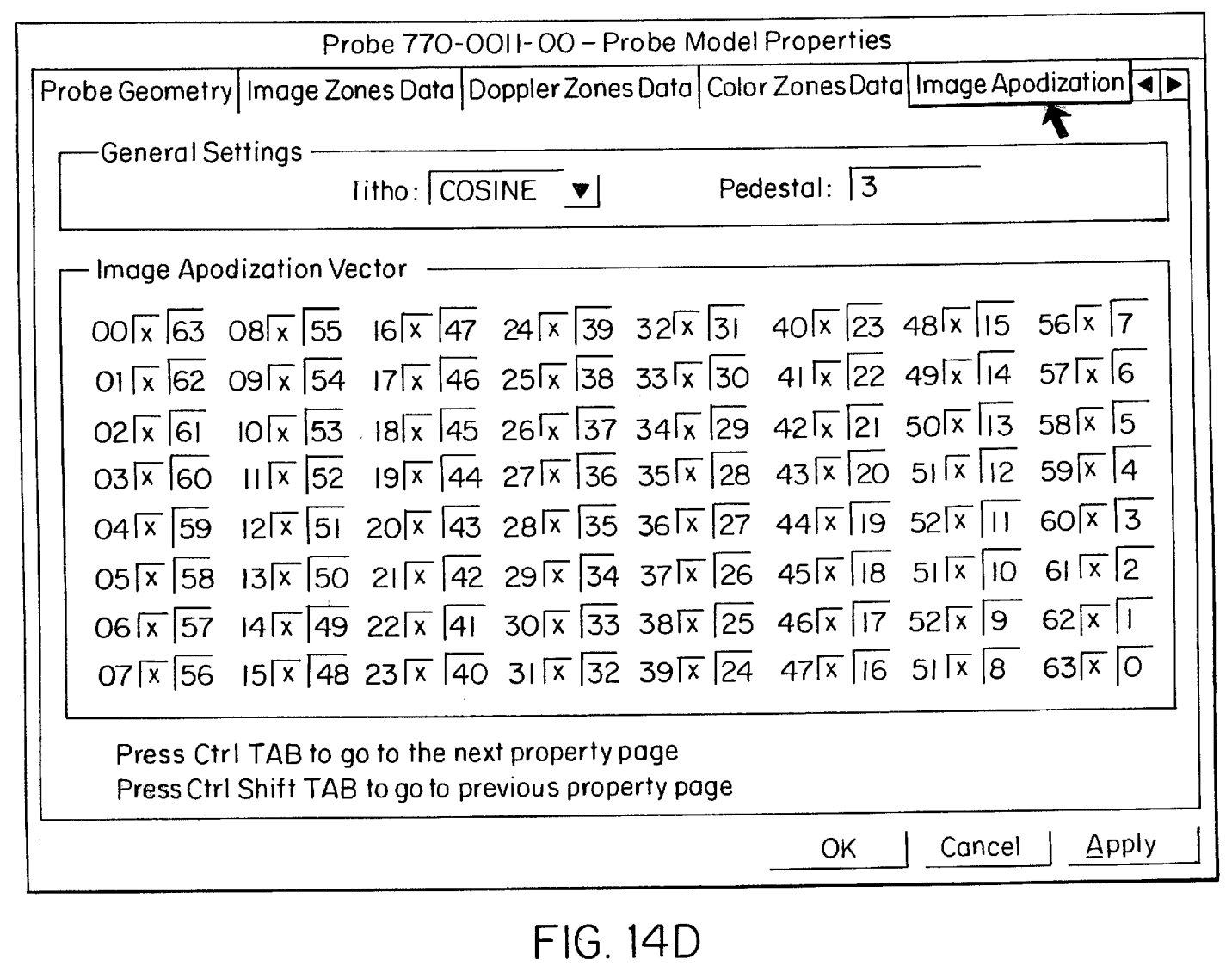

FIG. 14D illustrates a dialog box for effecting the image apodization function 470. As illustrated, the operator can enter and view general settings 472 and vector information 474. The user can select active elements for array windowing (or apodization).

The probe specific property display 500 includes dialog boxes for entering probe specifics 510, image Field Of-View (FOV) data 520, doppler FOV data 530, and color FOV data 540. Through the probe specifics dialog box 510, the user can enter general settings 512, imaging static information 514, doppler static information 516, and FOV settings 518.

FIG. 15A illustrates a dialog box for entering, and viewing probe specific information. Any number of probes can be supported.

FIGS. 15B–15C illustrate dialog boxes for entering image FOV data 520. As illustrated, a user can enter general settings 522, breakpoint PGC data 524, zone boundaries 526, and zone duration 528 data. Dialog boxes for the doppler and color FOV data displays 530,540 are similar and are all the entry of general settings 532, 542, breakpoint TGC data 534, 544, and PRF data 536, 546.

Figure 16:
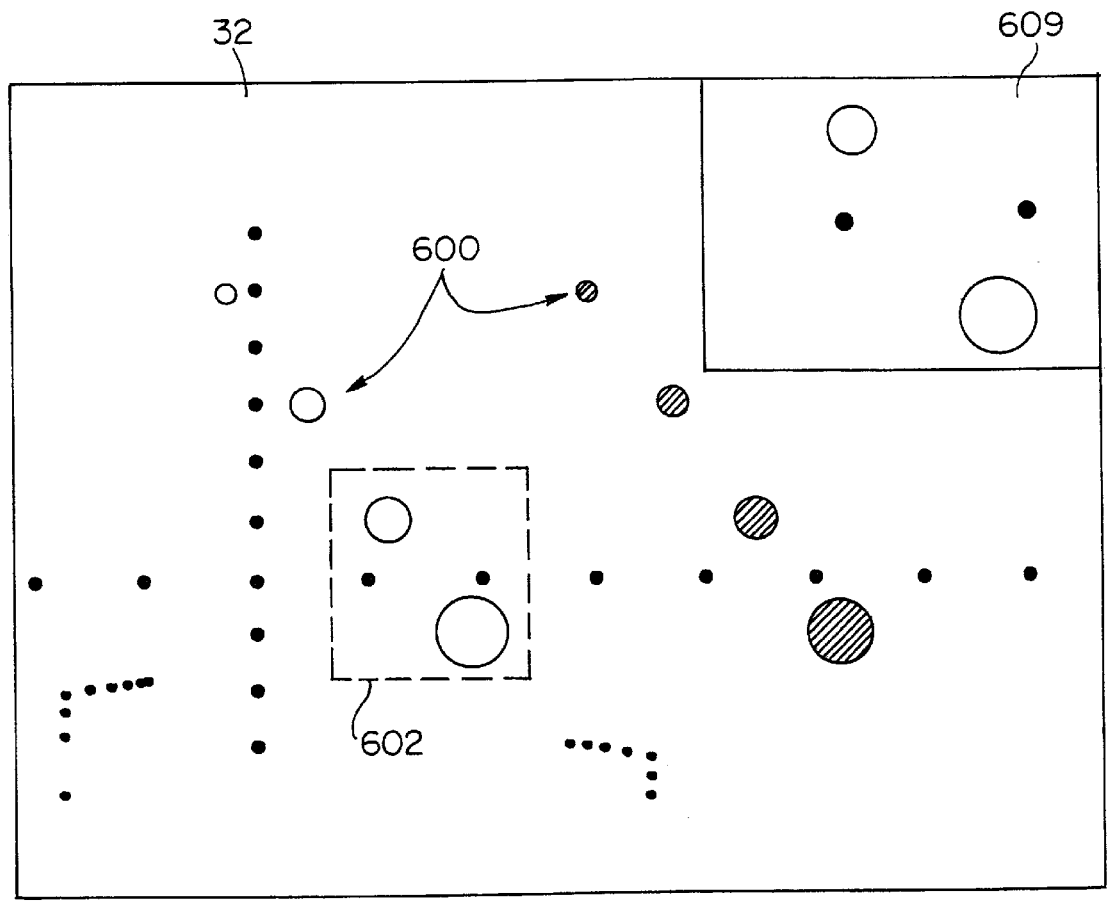
FIG. 16 illustrates imaging and display operations of a preferred embodiment of the invention.

FIG. 16 illustrates the zoom feature of a preferred embodiment of the imaging system in accordance with the invention. In this particular illustration detailed features of a phantom, or internal anatomical features 600 of a patient that are shown on screen 32, can be selected and enlarged within or over a display window. In this particular example, a region 602 is selected by the user and is enlarged at window 604. A plurality of such regions can be simltuaneously enlarged and shown on screen 32 in separate or overlying windows. If two scan heads are in use, different views can be shown at the same time, or previously recorded images can be recalled from memory and displayed beside an image presented in real time.

While this invention has been particularly shown and described with references to preferred embodiments thereof, it will be understood by those skilled in the art that various changes in form and details may be made therein without departing from the spirit and scope of the invention as defined by the appended claims.

We claim:

1. A method of converting ultrasound scan data into a display format for a medical imaging system, comprising the steps of:

providing an input array of input data from an ultrasonic device having a transducer array; and providing a remap array;

spatially dithering the input data with the remap array to convert the input data into an output array of output data.

2. The method of claim 1 wherein the step of spatial dithering comprises rounding position data from arbitrary precision values to integer values with remainder values.

3. The method of claim 2 wherein the step of spatial dithering further comprises propagating remainder values through the output data.

4. The method of claim 1 wherein the step of spatial dithering comprises:

calculating a first position in the output array from a first value in the input array; and using the first position, calculating a second position in the output array.

5. The method of claim 4 wherein the first and second positions represent adjacent display pixel locations.

6. The method of claim 1 wherein the step of spatial dithering is performed in a general purpose computer.

7. The method of claim 6 wherein the general purpose computer is a portable computer.

8. The method of claim 1 wherein the step of providing an input array further comprises receiving the input data from the ultrasonic device in polar coordinates.

9. The method of claim 1 further comprising mapping the output array to the input array.

10. The method of claim 9 wherein the step of mapping comprises initializing a remap array based on changes to the display format.

11. The method of claim 1 further comprising providing a scan conversion circuit that spatially dithers the input data.

12. A method for converting ultrasound scan data of a patient to a display format comprising:

providing an input array of input ultrasound data received from a transducer probe;

providing a personal computer, the personal computer being programmed with a remap array to perform conversion of the input ultrasound data; and converting the input array of input ultrasound data into an output array having a display format with the remap array.

13. The method of claim 12 further comprising converting a plurality of frames of input ultrasound data at a rate of at least 20 frames per second.

14. The method of claim 13 further comprising converting at a rate of about 30 frames per second or more.

15. An ultrasound imaging system comprising:

a transducer array that transmits and receives ultrasound signals;

a beamforming circuit electrically connected to the transducer array and that forms an electronic representation of an object to be imaged;

a programmable data processing system that receives the electronic representation, the computer being programmed with a remap array to perform spatially dithered scan conversion of the electronic representation to a display format.

16. The system of claim 15 wherein the programmable data processing system is a personal computer.

17. The system of claim 15 wherein the programmable data processing system is a portable computer having a keyboard and a liquid crystal display.

18. The system of claim 15 wherein the programmable data processing system is a palmtop computer.

19. The system of claim 15 further comprising an interface circuit.

20. The system of claim 15 further comprising a handheld housing including the transducer array and the beamforming circuit.

21. The method of claim 1 further comprising the step of smoothing the output data with a filter.

22. The method of claim 21 further comprising applying a matched filter to smooth the output data, the filter being dependent upon a distance between spatially dithered points of an object to be imaged.

23. The method of claim 1 further comprising providing a graphical user interface to control the display of an image.

24. The method of claim 23 further comprising providing a first image window and a second image window.

25. The method of claim 23 further comprising providing an enlarged view of the image.

26. The method of claim 23 further comprising rotating the image.

27. The method of claim 1 further comprising the step of scanning a first zone of an object to be imaged, scanning a second zone of the object, constructing an image of the second zone and subsequently constructing an image of the first zone.

28. The method of claim 10 further comprising providing text in the remap array to be displayed on an image of an object.

29. The system of claim 19 wherein the interface circuit is connected to the beamforming circuit with firewire.

30. The system of claim 19 further comprising a differential driver and receiver to connect the beamforming circuit to the interface.

31. A method for converting ultrasound scan data of a patient to a display format comprising:

providing an input array of input ultrasound data;

providing a personal computer, the personal computer being programmed to perform conversion of the input ultrasound data; and converting a plurality of frames of input ultrasound data at a rate of at least 20 frames per second, the input array of input ultrasound data being converted into an output array having a display format.

32. The method of claim 31 further comprising converting at a rate of about 30 frames per second or more.

33. The method of claim 31 further comprising the step of smoothing the output data with a filter.

34. The method of claim 33 further comprising applying a matched filter to smooth the output data, the filter being dependent upon a distance between spatially dithered points of an object to be imaged.

35. The method of claim 31 further comprising providing a graphical user interface to control the display of an image.

36. The method of claim 35 further comprising providing a first image window and a second image window.

37. The method of claim 35 further comprising providing an enlarged view of the image.

38. The method of claim 35 further comprising rotating the image.

39. The method of claim 31 further comprising the step of scanning a first zone of an object to be imaged, scanning a second zone of the object, constructing an image of the second zone and subsequently constructing an image of the first zone.

40. The method of claim 31 further comprising providing text in the remap array to be displayed on an image of an object.

41. The system of claim 31 wherein the interface circuit is connected to the beamforming circuit with firewire.

42. The system of claim 31 further comprising a differential driver and receiver to connect the beamforming circuit to the interface.

* * * * *